United States Patent [19]

Keene et al.

[11] Patent Number: 5,444,149

[45] Date of Patent: Aug. 22, 1995

[54] METHODS AND COMPOSITIONS USEFUL IN THE RECOGNITION, BINDING AND EXPRESSION OF RIBONUCLEIC ACIDS INVOLVED IN CELL GROWTH, NEOPLASIA AND IMMUNOREGULATION

[75] Inventors: Jack D. Keene, Durham, N.C.; Peter H. King, Birmingham, Ala.

[73] Assignee: Duke University, Durham, N.C.

[21] Appl. No.: 881,075

[22] Filed: May 11, 1992

[51] Int. Cl.⁶ .............................................. C07K 14/00
[52] U.S. Cl. ..................................... 530/300; 530/350
[58] Field of Search .............................. 530/350, 300

[56] References Cited

PUBLICATIONS

Szuho et al. Cell 67:325, 1991.
Levori et al. TIBS 16:214, 1991 (Jun.).
Cobianchi et al. JBC 261(8):3536, 1986.
Rohinow et al. Science 242:1570, 1988.
Patent Cooperation Treaty (Search Report).
PCT Written Option.
The Journal of Biological Chemistry, vol. 261, No. 8 Mar. 15, pp. 3536–3543, (1986).
Annu. Rev. Genet., vol. 24, pp. 519–541, 1990, J. A. Atwater, et al., "Regulated mRNA Stability".
Science, vol. 240, pp. 889–895, May 13, 1988, R. M. Evans, "The Steroid and Thyroid Hormone Receptor Superfamily".
Biochemistry, vol. 19, pp. 4674–4682, 1980, R. L. Karpel, et al., "Physical Studies of the Interaction of a Calf Thymus Helix-Destabilizing Protein with Nucleic Acids".
Cell, vol. 34, pp. 865–879, Oct. 1983, K. Zinn, et al., "Identification of Two Distinct Regulatory Regions Adjacent to the Human Beta-Interferon Gene".
Cell, vol. 45, pp. 827–835, Jun. 20, 1986, A. B. Sachs, et al., "A Single Gene from Yeast for both Nuclear and Cytoplasmic Polyadenylate-Binding Proteins: Domain Strucutre and Expression".
Cell, vol. 46, pp. 659–667, Aug. 29, 1986, G. Shaw, et al., "A Conserved Au Sequence from the 3' Untranslated Region of GM-CSF mRNA Mediates Selective mRNA Degradation".
Cell, vol. 51, pp. 211–220, Oct. 23, 1987, C. C. Query, et al., "A Human Autoimmune Protein Associated with U1 RNA Contains A Region of Homology that is Cross-Reactive with Retrovial p30$^{gag}$ Antigen".
Cell, vol. 52, pp. 1–3, Jan. 15, 1988, R. M. Evans, et al., "Zinc Fingers: Gilt by Association".
Cell, vol. 52, pp. 221–228, Jan. 29, 1988, J. Wilusz, et al., "A 64 kd Nuclear Protein Binds to RNA Segments that Include the AAUAAA Polyadenylation Motif".
Cell, vol. 55, pp. 537–540, Nov. 18, 1988, M. Levine, et al., "Homeobox Proteins as Sequence-Specific Transcription Factors".
Cell, vol. 55, pp. 1025–1035, Dec. 23, 1988, H. Amrein, et al., "The Sex-Determining Gene tra-2 of Drosophila Encodes A Putative RNA Binding Protein".
Cell, vol. 55, pp. 1037–1046, Dec. 23, 1988, L. R. Bell, et al., "Sex-Lethal, A Drosophila Sex Determination Switch Gene, Exhibits Sex-Specific RNA Splicing and Sequence Similarity to RNA Binding Proteins".
Cell, vol. 56, pp. 1011–1018, Mar. 24, 1989, T. J. Goralski, et al., "The Sex Determination Locus Transformer-2 of Drosophila Encodes A Polypeptide with Similarity to RNA-Binding Proteins".
Cell, vol. 57, pp. 89–101, Apr. 7, 1989, C. C. Query, et al., "A Common RNA Recognition Motif Identified (List continued on next page.)

*Primary Examiner*—Suzanne E. Ziska
*Attorney, Agent, or Firm*—Oblon, Spivak, McClelland, Maier, & Neustadt

[57] ABSTRACT

A peptide, Hel-N1 (SEQ ID NO: 2), which can bind to a 3'-untranslated mRNA sequence (which encompasses the "instability sequence") that is uniquely present in the messenger RNAs that encode oncoproteins and lymphokines, and mediates the specific destruction of the messenger RNAs, is described. Full-length Hel-N1 is capable of suppressing cell growth and causing cellular differentiation. Hel-N1 (SEQ ID NO: 2) possess three RNA recognition motifs. One of these forms an RNA-binding domain which, when transfected alone into cells, causes them to undergo rapid growth.

1 Claim, 10 Drawing Sheets

PUBLICATIONS

Within A Defined U1 RNA Binding Domain of the 70K U1 snRNP Protein".

Cell, vol. 58, pp. 231–232, Jul. 28, 1989, M. Rebagliati, "An RNA Recognition Motif in the Bicoid Protein".

Cell, vol. 58, pp. 857–867, Sep. 8, 1989, A. B. Sachs, et al., "The Poly(A) Binding Protein is Required for Poly(A) Shortening and 60s Ribosomal Subunit–Dependent Translation Initiation".

Cell, vol. 67, pp. 325–333, Oct. 18, 1991, A. Szabo, et al., "HuD, A Paraneoplastic Encephalomyelitis Antigen, Contains RNA–Binding Domains and is Homologous to Elav and Sex–Lethal".

Current Option in Cell Biology, vol. 1, pp. 1148–1153, 1989, D. W. Cleveland, "Gene Regulation Through Messenger RNA Stability".

The EMBO Journal, vol. 5, No. 12, pp. 3209–3217, 1986, H. Theissen, et al., "Cloning of the Human cDNA for the U1 RNA–Associated OK Protein".

The EMBO Journal, vol. 6, No. 12, pp. 3841–3848, 1987, P. T. G. Sillekens, et al., "cDNA Cloning of the Human U1 snRNA–Associated A Protein: Extensive Homology Between U1 and U2 snRNP–Specific Proteins".

The EMBO Journal, vol. 7, No. 11, pp. 3519–3529, 1988, M. S. Swanson, et al., "RNA Binding Specificity of the hnRNP Proteins: A Subset Bind to the 3' End of Introns".

The EMBO Journal, vol. 7, No. 13, pp. 4311–4321, 1988, M. Etzerodt, et al., "Structure and Expression of a Xenopus Gene Encoding an snRNP Protein" (U1 70K).

The EMBO Journal, vol. 8, No. 13, pp. 4163–4170, 1989, D. Scherly, et al., "Identification of the RNA Binding Segment of Human U1 A Protein and Definition of its Binding Site on U1 snRNA".

The EMBO Journal, vol. 9, No. 11, pp. 3533–3538, 1990, R. T. Fremeau, et al., "In Situ Analysis of Myelin Basic Protein Gene Expression in Myelin–Deficient Oligodendrocytes: Antisense hnRNA and Readthrough Transcription".

Eur. J. Biochem., vol. 179, pp. 541–548, 1989, M. Sapp, et al., "Characterization of a 48–kDa Nucleic–Acid Binding Fragment of Nucleolin".

FEBS Letters, vol. 257, No. 2, pp. 373–376, Nov., 1989, A. G. Ghetti, et al., "Secondary Structure Prediction for RNA Binding Domain in RNP Proteins Identifies Beta Alpha Beta as the Main Structural Motif".

Genes & Development, vol. 3, pp. 324–333, 1989, M. Caizergues–Ferrer, et al., "Nucleolin from Xenopus Laevis: cDNA Cloning and Expression During Development".

Journal Of Autoimmunity, vol. 2, pp. 329–334, 1989, J. D. Keene, "Molecular Structure of the La and Ro Autoantigens and their Use In Autoimmune Diagnostics".

The Journal of Biological Chemistry, vol. 259, No. 9, pp. 5907–5914, May 10, 1984, I. Pettersson, et al., "The Structure of Mammalian Small Nuclear Ribonucleoproteins".

The Journal of Biological Chemistry, vol. 261, No. 8, pp. 3536–3543, Mar. 15, 1986, F. Cobianchi, et al., "Structure of Rodent Helix–Destabilizing Protein Revealed by cDNA Cloning".

The Journal of Biological Chemistry, vol. 262, No. 23, pp. 10922–10925, Aug. 15, 1987, B. Bugler, et al., "RNA Binding Fragments from Nucleolin Contain the Ribonucleoprotein Consensus Sequence".

The Journal of Biological Chemistry, vol. 262, No. 35, pp. 17126–17137, Dec. 15, 1987, A. Kumar, et al., "Purification and RNA Binding Properties of a C–Type hnRNP Protein from HeLA Cells".

The Journal of Biological Chemistry, vol. 263, No. 2, pp. 1063–1071, Jan. 15, 1988, F. Cobianchi, et al., "Mammalian Heterogeneous Nuclear Ribonucleoprotein Complex Protein A1".

The Journal of Biological Chemistry, vol. 263, No. 7, pp. 3307–3313, Mar. 5, 1988, B. M. Merrill, et al., "Phenylalanines that are Considered Among Several RNA–Binding Proteins Form Part of a Nucleic Acid––Binding Pocket in the A1 Heterogeneous Nuclear Ribonucleoprotein".

The Journal of Biological Chemistry, vol. 263, No. 26, pp. 12824–12827, Sep. 15, 1988, J. H. Chang, et al., "cDNA and Deduced Primary Structure of Rat Protein B23, A Nucleolar Protein Containing Highly Conserved Sequences".

The Journal of Biological Chemistry, vol. 263, No. 34, pp. 18043–18051, Dec. 5, 1988, J. C. Chambers, et al., "Genomic Structure and Amino Acid Sequence Domains of the Human La Autoantigen".

Journal of Molecular Biology, vol. 200, pp. 627–638, 1988, H. M. Bourbon, et al., "Structure of the Mouse Nucleolin Gene, The Complete Sequence Reveals that Each RNA Binding . . .".

Journal of Molecular Biology, vol. 207, pp. 491–503, (List continued on next page.)

PUBLICATIONS

1989, G. Biamonti, et al., "Isolation of an Active Gene Encoding Human hnRNP Protein A1".

Molecular and Cellular Biology, vol. 5, No. 8, pp. 1993-1996, Aug., 1985, A. B. Sachs, et al., "Nuclear Polydenylate-Binding Protein".

Molecular and Cellular Biology, vol. 6, No. 8, pp. 2932-2943, Aug., 1986, S. A. Adam, et al., "mRNA Polyadenylate-Binding Protein: Gene Isolation and Sequencing and Identification of a Ribonucleoprotein Consensus Sequence".

Molecular and Cellular Bilogy, vol. 7, No. 5, pp. 1731-1739, May, 1987, M. S. Swanson, et al., "Primary Structure of Human Nuclear Ribonucleoprotein Particle C . . . ".

Molecular and Cellular Biology, vol. 7, No. 8, pp. 2947-2955, Aug., 1987, A. Y. S. Jong, et al., "Saccharomyces Cerevisiae SSB1 Protein and its Relationship to Nucleolar RNA-Binding Proteins".

Molecular and Cellular Biology, vol. 7, No. 9, pp. 3268-3276, Sep., 1987, A. B. Sachs, et al., "A Single Domain of Yeast Poly(A)-Binding Protein is Necessary and Sufficient for RNA Binding and Cell Viability".

Molecular and Cellular Biology, vol. 7, No. 12, pp. 4513-4521, Dec., 1987, T. R. Jones, et al., "Rapid Cytoplastic Turnover of c-myc mRNA: Requirement of the 3'Untranslated Sequences".

Molecular and Cellular Biology, vol. 8, No. 5, pp. 2237-2241, May, 1988, M. S. Swanson, et al., "Classification and Purification of Proteins of Heterogeneous Nuclear Ribonucleoprotein Particles by RNA-Binding Specificities".

Molecular and Cellular Biology, vol. 9, No. 7, pp. 2975-2982, Jul., 1989, C. Lutz-Freyermuth, et al., "The U1 RNA-Binding Site of the U1 Small Nuclear Ribonucleoprotein (snRNP)-Associated A Protein Suggests A Similarity with U2 snRNPs".

Molecular and Cellular Biology, vol. 9, No. 11, pp. 4872-4881, Nov., 1989, C. C. Query, et al., "A Specific 31-Nucleotide Domain of U1 RNA Directly Interacts with the 70K Small Nuclear Ribonucleoprotein Component".

Molecular and Cellular Biology, vol. 10, No. 1, pp. 316-323, Jan., 1990, S. R. Haynes, et al., "the Drosophila Hrb98DE Locus Encodes Four Protein Isoforms Homologous to the A1 Protein of Mammalian Nuclear Ribonucleaoprotein Complexes".

Molecular and Cellular Biology, vol. 11, No. 4, pp. 1829-1839, Apr., 1991, R. C. Bentley, et al., "Recognition of U1 and U2 Small Nuclear RNAs Can Be Altered by a 5-Amino-Acid Segment in the U2 Small Nuclear Ribonucleoprotein Particle (snRNP) B" Protein . . . ".

Molecular and Cellular Biology, vol. 11, No. 5, pp. 2460-2466, May, 1991, G. Brewer, "An A+U-Rich Element RNA-Binding Factor Regulates c-myc mRNA Stability In Vitro".

Molecular and Cellular Biology, vol. 11, No. 6, pp. 3355-3364, Jun., 1991, E. Vakalopoulou, et al., "A 32-Kilodalton Protein Binds to Au-Rich Domains in the 3' . . . ".

Nature, vol. 336, pp. 522-524, Dec. 8, 1988, M. Robertson, "Homoeo Boxes, Pou Proteins and the Limits to Promiscuity".

Nature, vol. 340, pp. 521-524, Aug., 17, 1989, B. S. Baker, "Sex In Flies: The Splice of Life".

Nature, vol. 344, pp. 461-463, Mar. 29, 1990, K. Inoue, et al., "Binding of the Drosophila Sex-Lethal Gene Product to the Alternative Splice Site of Transformer Primary Transcript".

Nature, vol. 345, pp. 502-506, Jun. 7, 1990, D. Scherly, et al., "Major Determinants of the Specificity of Interaction Between Small Nuclear Ribonucleoproteins U1A and U2B". . .

Neurology, vol. 38, pp. 1018-1026, Jul., 1988, N. E. Anderson, et al., "A Variant of the Anti-Purkinje Cell Antibody in a Patient with Paraneoplastic Cerebellar Degeneration".

Nucleic Acids Research, vol. 15, No. 12, pp. 4771-4786, 1987, T. Grange, et al., "Human mRNA Polyadenylate Binding Protein: Evolutionary Conservation of a Nucleic Acid Binding Motif".

Nucleic Acids Research, vol. 15, No. 24, pp. 10373-10391, 1987, A. S. Spritz, et al., "The Human U1-70K snRNP Protein: cDNA Cloning, Chromosomal Localization, Expression, Alternative Splicing and RNA-Binding".

Nucleic Acids Research, vol. 13, No. 16, 1985, pp. 5805-5816, 1985, B. LaPeyre, et al., "Cloning of cDNA Encoding A 100 kDa Nucleolar Protein (Nucleoline) of Chinese Hamster Ovary Cells".

Nucleic Acids Research, vol. 13, No. 18, pp. 6577-6590, (List continued on next page.)

PUBLICATIONS

1985, M. Pandolfo, et al., "Single Stranded DNA Binding Proteins Derive from hnRNP Proteins by Proteolysis in Mammalian Cells".

Nucleic Acids Research, vol. 19, No. 18, pp. 4931–4936, D. E. Tsai, et al., "U1-snRNP-A Protein Selects a Ten Nucleotide Consensus Sequence from a Degenerate RNA Pool Presented in Various Structural Contexts".

Annals of Neurology, vol. 27, No. 5, pp. 544–552, May 1990, J. Dalmau, et al., "Detection of the Anti-Hu Antibody in the Serum of Patients with Small Cell Lung Cancer—A Quantitative Western Blot Analysis".

Proc. Natl. Acad. Sci. USA, vol. 76, No. 11, pp. 5495–5499, Nov., 1979, M. R. Lerner, et al., "Antibodies to Small Nuclear RNAs Complexed with Proteins . . .".

Proc. Natl. Acad. Sci. USA, vol. 82, pp. 2115–2119, Apr. 1985, J. C. Chambers, et al., "Isolation and Analysis of cDNA Clones Expressing Human Lupus La Antigen".

Proc. Natl. Acad. Sci. USA, vol. 82, pp. 4987–4991, Aug., 1985, F. Meulink, et al., "Removal of a 67-Base-Pair Sequence in the Noncoding Region of Protooncogene fos Converts it to a Transforming Gene".

Proc. Natl. Acad. Sci. USA, vol. 83, pp. 1670–1674, Mar., 1986, D. Caput, et al., "Creation of a Common Nucleotide Sequence in the Translated Region of mRNA Molecules Specifying Mammatory Mediators".

Proc. Natl. Acad. Sci. USA, vol. 83, pp. 2007–2011, Apr., 1986, T. Y. Nakagawa, et al., "Molecular Cloning of cDNA for the Nuclear Ribonucleoprotein Particle C Proteins: A Conserved Gene Family".

Proc. Natl. Acad. Sci. USA, vol. 84, pp. 1819–1823, Apr., 1987, S. R. Haynes, et al., "Pen Repeat Sequences are GGN Clusters and Encode A Glycine-Rich Domain in Drosophila cDNA Homologous to the Rat Helix Destabilizing Protein".

Proc. Natl. Acad. Sci. USA, vol. 84, pp. 2421–2425, Apr., 1987, W. J. Habets, et al., "Analysis of a cDNA Clone Expressing a Human Autoimmune Antigen . . .".

Proc. Natl. Acad. Sci. USA, vol. 84, pp. 4552–4556, Jul., 1987, E. J. Dropcho, et al., "Cloning of a Brain Protein Identified by Autoantibodies from a Patient With Paraneoplastic Cerebellar Degeneration".

Proc. Natl. Acad. Sci. USA, vol. 85, pp. 2538–2542, Apr., 1988, A. J. Dombroski, et al., "Structure of a p Factor: An RNA-Binding Domain and a Separate Region . . .".

Proc. Natl. Acad. Sci. USA, vol. 85, pp. 9479–9483, Dec., 1988, S. L. Deutscher, et al., "Molecular Analysis of the 60-kDa Human Ro Ribonucleoprotein".

Proc. Natl. Acad. Sci. USA, vol. 86, pp. 9788–9792, Dec., 1989, C. G. Burd, et al., "Primary Structures of the Heterogeneous Nuclear Ribonucleoprotein A2, B1, and C2 Proteins . . .".

Proc. Natl. Acad. Sci. USA, vol. 87, pp. 3082–3086, Apr., 1990, M. A. Garcia-Blanco, et al., "A Mammalian Protein of 220 kDa Binds Pre-mRNAs . . .".

Proc. Natl. Acad. Sci. USA, vol. 87, pp. 6393–6397, Aug., 1990, C. Lutz-Freyermuth, et al., "Quantitative Determination That One of Two Potential RNA-Binding Domains of the A Protein Component of the U1 Small Nuclear Ribonucleoprotein Complex . . .".

Proc. Natl. Acad. Sci. USA, vol. 89, pp. 1296–1300, Feb., 1992, V. E. Myer, et al., "Viral Small Nuclear Ribonucleoproteins Bind a Protein Implicated in Messenger RNA . . .".

TIBS, vol. 13, pp. 86–91, Mar., 1988, G. Dreyfuss, et al., "Heterogeneous Nuclear Ribonucleoprotein Particles and the Pathway of mRNA Formation".

Science, vol. 242, pp. 1570–1572, Dec. 1988, S. Robinow, et al., "The Elav Gene Product of Drosophila, Required in Neurons, Has Three RNP Consensus Motifs".

Science, vol. 246, pp. 664–666, Nov. 1989, J. S. Malter, "Identification of an UUUA-Specific Messenger RNA Binding Protein".

TIBS, vol. 16, pp. 214–220, Jun., 1991, D. J. Kenan, et al., "RNA Recognition: Towards Identifying Determinants of Specificity".

Molecular and Cellular Biology, vol. 9, No. 10, pp. 4179–4186, Oct., 1989, C. S. Surowy, et al., "Direct, Sequence-Specific Binding of the Human U1-70K Ribonucleoprotein Antigen Protein to Loop I of U1 Small Nuclear RNA".

Genes & Development, pp. 431–437, R. J. Bandziulis, et al., "RNA-Binding Proteins as Developmental Regulators".

Developmental Biology, vol. 126, pp. 294–303, 1988, S. Robinow, et al., "The Locus Elav of Drosophila Melanogaster is Expressed in Neurons at All Developmental Stages".

FIG. 1A

```
elav   MDFIMANT- - - - - - - -GAGGGVDTQAQLMQSAAAAAAVAATNAAA         37
Hel-N1 -M- -E- -T- - - -QLSI- - - - - - - - - - -NGP-TCNN-T- -A-      15
K3     MVEGQTAVQQQQQQPSGAGGASGVGSTTGSAGGPATANNVINSQA                   45 elav   APVQNAAAVAAAAQLQQQQVQQAILQVQQQQTQQAVAAAAAAVTQ                   82
Hel-N1 - -NGPT- - - - - - - - - - -TIN- - - - - - - -NNCSS- -PVDSGNT- -  34
K3     QTNGGTTATTTAAAGAGSTTNAAVGQATANNAASNNNNNNNTNN                    90 elav   QLQQQQQAVVAQQAVVQQQQQAAAAVVQQAAVQQAAVVPQPQQAQP                  127
Hel-N1 - - - - - - - - - - - -E-DS- - - - - - - - - - - - - - - - - - - 32
K3     NNNNATANNNNNNEPDP- - - - - - - - - - - - - - - - - - - - - - - 108 elav   NTNGNAGSGSQNGSNGSTETRTNLIVNYLPQTMTEDEIRSLFSSV                   172
Hel-N1 - - - - - - - - - - - - - - -KT-L-V-N-L-P-Q-MTQEELKSLFGSI-          62
K3     - - - - - - - - - - - - - - -KT-NLIVNYLPQTMSQDEIRSLFVSF            133 elav   GEIESVKLIRDKSQVYIDPLNPQAPSKGQSLGSGTVKYVRPQDAE                   217
Hel-N1 - -GEIES-S-CKLV-RDKIT- - - - - - - - - -G- -S-G-TVKY- - -IDPKDAE-  94
K3     - -GEVESCKLIRDKVT- - - - - - - - - -GQSLGSGTVKY-VKQEDAE             165 elav   QAVNVLNGLRLQNKTIIKVSFARPSSDAIKGANLYVSGLPKTMTQQ                  262
Hel-N1 KA-INTL-NG-LRL-Q-TK-IT- -K-V-S-YARPS-SASIRDAN-LYVSGLP-KTMTQK   139
K3     KAINALNGLRLQNKTIIKVSIARPSSESIKGANLYVSGLPKNMTQS                  210
```

FIG. 1B

```
elav   ELEAIFAPFGAIIITSRILQNAGND----TQTKGVGFIRFDKREEA  303
Hel-N1 -L-EQLFSQYGRIIITSRILVDQVT----GISRGVGFIRFDKIREA  179
K3     DLESLFSPYGKIIITSRILCDNITDEHAAGLSKGVGFIRFDQRFEA  255 elav   TRAIIALNGTTPSSCTDPIVVKFSNTPGSTSKIIQPQLPAFLNPQ   348
Hel-N1 EAIKGLNGQKPPGATEPIT-VKF-ANNPSQKTNQAILSQLYQSP-N  223
K3     DRAIKELNGTTPKNSTEPIT-VKF-ANNPSSNKNSMQPLAAYIAPQN 300 elav   LVRRIGGAMHTPVNKGLARFSPMAGDMLDVMLPNGLGAAAAAATI  393
Hel-N1 -R--R-YP----GPLAQQAQRFLDNLLNMAYGVKRFSPMTIDG-   259
K3     TRGGRAFPANAAAAGA-AAAAAAIHPNAGRYSSVISRYSPLTSDL  345 elav   LASGPGGAYP-----IFIYNLAPETEEAAL WQLFGPFGAVQS    430
Hel-N1 MTSLAGINIPGHPGTGWC-IF-V-YNL--APDADESIL-W-Q-MFGPF-GAVTN  304
K3     IT-NGMIQGNTIASSGWCIF-V-YNL-APETEENVL-WQLFGPFGAVQS  389 elav   VKIVKDPITNQCKGYGFVSMTNYDEAAMAIRALNGYTMGNRVLQV  475
Hel-N1 -V-KVIRDFNTN-K-C-GF-VTM--N-YDE-A-AMAIRSL-NGYRLGDRVLQ-  349
K3     -VKVIRDLQSNKCKGFVTMTNYEEAVLAIQSLNGYTLGNRVLQV  434 elav   SFKTNK-AK---  483
Hel-N1 S-SFKTNK-THKA-  359
K3     -SFKTNKNKQT  444
```

| SELECTED Hel-N1 RNA-BINDING SEQUENCES | FOUND IN mRNA INSTABILITY REGIONS |
|---|---|
| AUUUA | GM-CSF, α-β-γIFN, IL1-2-3, c-myc, c-myb |
| UUAUUUAUU | TNF, c-IFN, GM-CSF |
| AUUUUUA | βIFN, c-myb, c-fos, IgG1-IF, IL-2 |
| AUUUUA | βIFN, c-myc, IL-2, c-fos, c-myb |
| AUUUUC | βIFN |
| GUUUUA | c-myc, c-fos |
| CUUUUA | IFN, c-myc |
| AUUUUUUUC | c-myc |
| AUUUG | c-myb, c-myc |
| AUUUC | c-sis |
| CUUUUA | c-sis |
| CUUUA | IL-2 |

*FIG. 4*

```
                                          40                              80                               120
                                          *                               *                                *
     CCAATAGTAGTCATTTAAATATATTCTGAAATCTTTG CAAATTTTAACAGAAGAGTCGAAGCTCTGCCGAGACCCAAT ATTTGCCAATAAGAATGTTATGATAATTAGCACCATGGA
                                                                                                           M  V  M  I  I  S  T  M  E  >

160                             200                              240
                                          *                               *                                *
     GGCTCAGGTGTCAAATGGTCCGACATCCAATACAAGCAAT GGACCCTCCAGCAACAACAGAAACTGTCCTTCTCCCATGC AAACAGGGCAACCACAGATGACAGCAAAACCAACCTCAT
     P  Q  V  S  N  G  P  T  S  N          G  P  S  S  N  N  R  N  C  P  S  P  M        Q  T  G  A  T  T  D  D  S  K  T  N  L  I  >

280                             320                              360
                                          *                               *                                *
     CGTCAACTATTTACCCAGAATATGACCCAAGAAGAATATTC AGGAGTCTCTTCGGGAGCATTGGTGAAATAGAATCCTGCA AACTGTGAGAGACAAAATTACAGGACAGAGTTTAGGGTA
     V  N  Y  L  P  Q  N  M  T  Q  E  E  F     R  S  L  F  G  S  I  G  E  I  E  S  C      K  L  V  R  D  K  I  T  G  Q  S  L  G  Y  >

400                             440                              480
                                          *                               *                                *
     TGGATTTGTTAACTATATATTGATCCAAAGGATGCAGAGAAA GCCATCAACACTTTAAATGGACTCAGACTCCAGACCAAAA CCATAAAGGTCTCATATGCCGTCCGAGCTCTGCCTCAAT
     G  F  V  N  Y  I  D  P  K  D  A  E  K     A  I  N  T  L  N  G  L  R  L  Q  T  K      T  I  K  V  S  Y  A  R  P  S  S  A  S  I  >

520                             560                              600
                                          *                               *                                *
     CAGGGATGCTAACCTCTATGTTAGCGGCCTTCCCAAAACC ATGACCCAGAAAGGACTGGAGCAACTTTCTCGCAATACG GCCGTATCATCACCTCACGAATCCTGGTTGATCAAGTCAC
     R  D  A  N  L  Y  V  S  G  L  P  K  T     M  T  Q  K  B  L  B  Q  L  F  S  Q  Y      G  R  I  I  T  S  R  I  L  V  D  Q  V  T  >

640                             680                              720
                                          *                               *                                *
     AGGAGTGTCCAGAGAGGGGTGGATCATCCGCTTTGATAAG AGGATTGAGGCAGAAGAAGCCATCAAAGGCTGAATGGCC AGAAGCCAGCGGTGCTACGGAACCGATTACTGTGAAGTT
     G  V  S  R  G  V  G  F  I  R  F  D  K     R  I  E  A  R  E  A  I  K  G  L  N  G      Q  K  P  S  G  A  T  E  P  I  T  V  K  P  >

760                             800                              840
                                          *                               *                                *
     TGCCAACAACCCCAGCAGAAGTCCAGCCCTGCTC TCCCAGTCTACCAGTCCCTACCAGGCTACCCAGTC CACTTCACCACCAGGCTCAGAGAGTTCAGGCTGGACAATTT
     A  N  N  P  S  Q  K  S  S  Q  A  L  L     S  Q  L  Y  Q  S  P  N  R  R  Y  P  G      P  L  N  N  Q  A  Q  R  F  L  D  N  L  >
```

FIG. 6A

```
                                                                      880                                 920                                 960
                                                                       *                                   *                                   *
GCTTAATATGGCCTATGGCGTAAAGAGACTGATGTCTGGA CCAGTCCCCCTTGTGCTTGTCCCCAGGTTCTCCCCAA TTACCATTGATGAATGACAAGCCTTGTGGGAATGAACAT
 L  N  M  A  Y  G  V  K  R  L  M  S  G    P  V  P  P  S  A  C  S  P  R  F  S  P    I  T  I  D  G  M  T  S  L  V  G  M  N  I >
                  1000                                1040                                1080
                    *                                   *                                   *
CCCTGGTGTCACACAGGAACTGGGTGGTGGCATCTTTGTCTAC AACCTGTCCCCCGATTCCGATGAGAGTGTCCTCTGGCAG TCTTTGGCCCCTTTGGAGCAGTGAACAACGTAAAGGTGAT
 P  G  N  T  G  T  G  W  S  I  F  V  Y     N  L  S  P  D  S  D  E  S  V  L  W  Q    L  F  G  P  F  G  A  V  N  N  V  K  V  I >
                  1120                                1160                                1200
                    *                                   *                                   *
TCGTGACTTCAACACCAACAAGTGCAAGGGATTCGGCTTT GTCACCATGACCAACTATGATGAGGCGGCCATGGCCATCG CCAGCCTCAACGGGTACCGCCTGGGAGACAGAGTGTTGCA
 R  D  F  N  T  N  K  C  K  G  P  G  F     V  T  M  T  N  Y  D  E  A  A  M  A  I    A  S  L  N  G  Y  R  L  G  D  R  V  L  Q >
                  1240                                1280                                1320
                    *                                   *                                   *
AGTTCCTTAAAACCAACAAAGCCCACAAGTCCTGAATT TCCCATTCTTACTTACTAAAATATATATAGAAATATATAC GAACAAAACACACGGCACACACACATACACGAAAG
 V  S  F  L  K  T  N  K  A  N  K  S >
                  1360                                1400                                1440
                    *                                   *                                   *
AGTTTCCTTAAAACCAACAAAGCCCACAAGTCCTGAATT ACTTATATAAGCCTAGTATTAAAACATTGGGT TATCCTGAGGTGTACCAGGAAAGGATTATAATGCTTAGAA

AGAGAGAAACAAACTTTTCAAGGCTTATATATTCAACCATGG
                    *
AAAAAAAAAAGAAAAAAAAAAAAAACAAAAAA
```

FIG. 6B

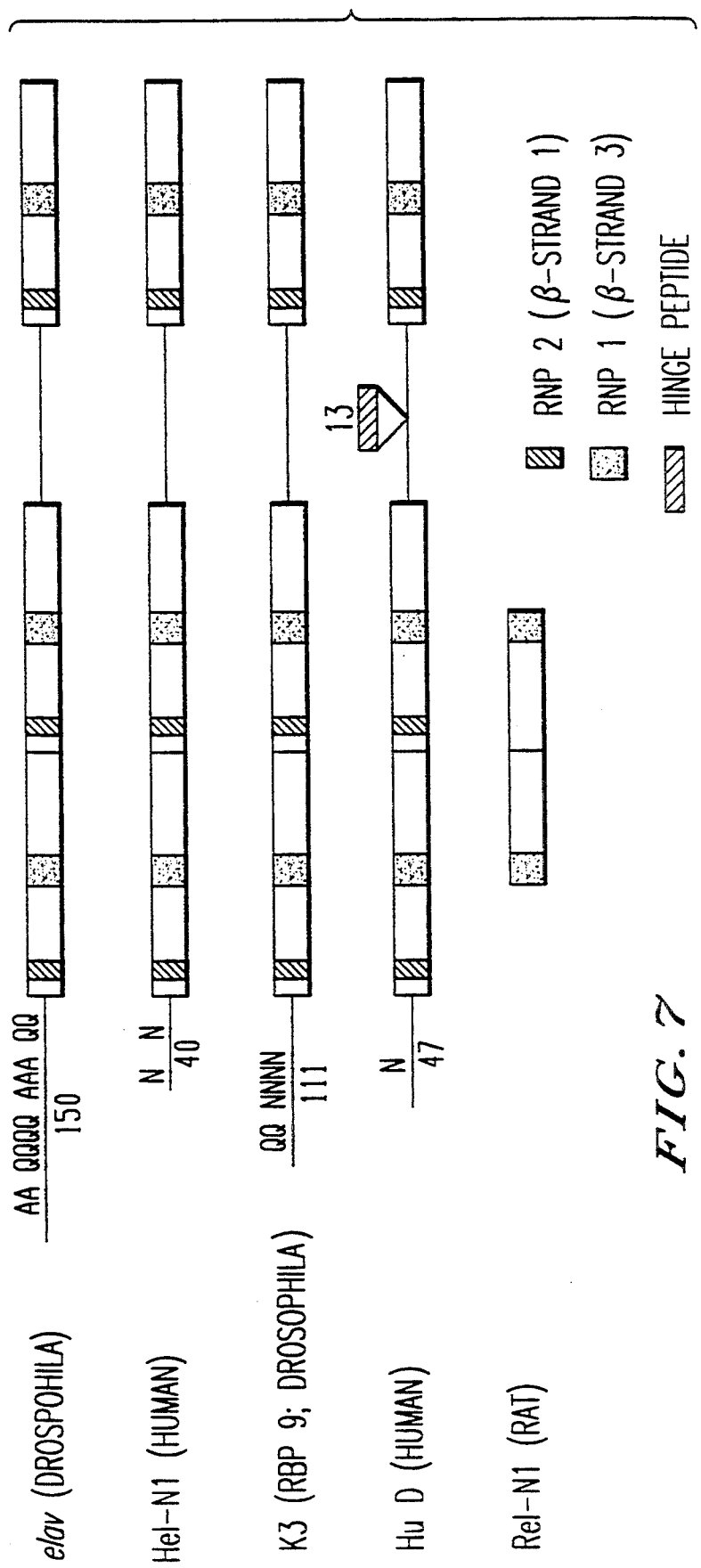

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
( A ) LENGTH: 485 amino acids
( B ) TYPE: amino acid
( D ) TOPOLOGY: unknown ( i i ) MOLECULE TYPE: protein ( x i ) SEQUENCE DESCRIPTION: SEQ ID NO:1:

```
Asp Cys Met Asp Phe Ile Met Ala Asn Thr Gly Ala Gly Gly Gly Val
 1               5                  10                  15

Asp Thr Gln Ala Gln Leu Met Gln Ser Ala Ala Ala Ala Ala Ala Val
                20                  25                  30

Ala Ala Thr Asn Ala Ala Ala Ala Pro Val Gln Asn Ala Ala Ala Val
             35                  40                  45

Ala Ala Ala Ala Gln Leu Gln Gln Gln Gln Val Gln Gln Ala Ile Leu
         50                  55                  60

Gln Val Gln Gln Gln Gln Thr Gln Gln Ala Val Ala Ala Ala Ala Ala
 65                  70                  75                  80

Ala Val Thr Gln Gln Leu Gln Gln Gln Gln Gln Ala Val Val Ala Gln
                 85                  90                  95

Gln Ala Val Val Gln Gln Gln Gln Gln Gln Ala Ala Ala Val Val Gln
                100                 105                 110

Gln Ala Ala Val Gln Gln Ala Val Val Pro Gln Pro Gln Gln Ala Gln
            115                 120                 125

Pro Asn Thr Asn Gly Asn Ala Gly Ser Gly Ser Gln Asn Gly Ser Asn
    130                 135                 140

Gly Ser Thr Glu Thr Arg Thr Asn Leu Ile Val Asn Tyr Leu Pro Gln
145                 150                 155                 160

Thr Met Thr Glu Asp Glu Ile Arg Ser Leu Phe Ser Ser Val Gly Glu
                165                 170                 175
```

| | | | | | | | | | | | | | | |
|---|---|---|---|---|---|---|---|---|---|---|---|---|---|---|
|Ile|Glu|Ser|Val|Lys|Leu|Ile|Arg|Asp|Lys|Ser|Gln|Val|Tyr|Ile|Asp|
| | | |180| | | |185| | | |  |190| | |

Pro Leu Asn Pro Gln Ala Pro Ser Lys Gly Gln Ser Leu Gly Xaa Gly
195 200 205

Phe Val Xaa Tyr Val Arg Pro Gln Asp Ala Glu Gln Ala Val Asn Val
210 215 220

Leu Asn Gly Leu Arg Leu Gln Asn Lys Thr Ile Lys Val Ser Phe Ala
225 230 235 240

Arg Pro Ser Ser Asp Ala Ile Lys Gly Ala Asn Leu Tyr Val Ser Gly
245 250 255

Leu Pro Lys Thr Met Thr Gln Gln Glu Leu Glu Ala Ile Phe Ala Pro
260 265 270

Phe Gly Ala Ile Ile Thr Ser Arg Ile Leu Gln Asn Ala Gly Asn Asp
275 280 285

Thr Gln Thr Lys Gly Val Gly Phe Ile Arg Phe Asp Lys Arg Glu Glu
290 295 300

Ala Thr Arg Ala Ile Ile Ala Leu Asn Gly Thr Thr Pro Ser Ser Cys
305 310 315 320

Thr Asp Pro Ile Val Val Lys Phe Ser Asn Thr Pro Gly Ser Thr Ser
325 330 335

Lys Ile Ile Gln Pro Gln Leu Pro Ala Phe Leu Asn Pro Gln Leu Val
340 345 350

Arg Arg Ile Gly Gly Ala Met His Thr Pro Val Asn Lys Gly Leu Ala
355 360 365

Arg Phe Ser Pro Met Ala Gly Asp Met Leu Asp Val Met Leu Pro Asn
370 375 380

Gly Leu Gly Ala Ala Ala Ala Ala Ala Thr Thr Leu Ala Ser Gly Pro
385 390 395 400

Gly Gly Ala Tyr Pro Ile Phe Ile Tyr Asn Leu Ala Pro Glu Thr Glu
405 410 415

Glu Ala Ala Leu Trp Gln Leu Phe Gly Pro Phe Gly Ala Val Gln Ser
420 425 430

Val Lys Ile Val Lys Asp Pro Thr Thr Asn Gln Cys Lys Gly Tyr Gly
435 440 445

Phe Val Ser Met Thr Asn Tyr Asp Glu Ala Ala Met Ala Ile Arg Ala
450 455 460

Leu Asn Gly Tyr Thr Met Gly Asn Arg Val Leu Gln Val Ser Phe Lys
465 470 475 480

Thr Asn Lys Ala Lys
485

(2) INFORMATION FOR SEQ ID NO:2:

(i) SEQUENCE CHARACTERISTICS:
    (A) LENGTH: 359 amino acids
    (B) TYPE: amino acid
    (D) TOPOLOGY: unknown (ii) MOLECULE TYPE: protein (xi) SEQUENCE DESCRIPTION: SEQ ID NO:2:

Met Glu Thr Gln Leu Ser Asn Gly Pro Thr Cys Asn Asn Thr Ala Asn
1 5 10 15

Gly Pro Thr Thr Ile Asn Asn Asn Cys Ser Ser Pro Val Asp Ser Gly
20 25 30

Asn Thr Glu Asp Ser Lys Thr Asn Leu Ile Val Asn Tyr Leu Pro Gln
35 40 45

Asn Met Thr Gln Glu Glu Leu Lys Ser Leu Phe Gly Ser Ile Gly Glu

-continued

|  |  |  |  |  | 50 |  |  |  |  | 55 |  |  |  |  | 60 |
|---|---|---|---|---|---|---|---|---|---|---|---|---|---|---|---|
| Ile | Glu | Ser | Cys | Lys | Leu | Val | Arg | Asp | Lys | Ile | Thr | Gly | Gln | Ser | Leu |
| 65 |  |  |  |  | 70 |  |  |  |  | 75 |  |  |  |  | 80 |
| Gly | Tyr | Gly | Phe | Val | Xaa | Tyr | Ile | Asp | Pro | Lys | Asp | Ala | Glu | Lys | Ala |
|  |  |  |  | 85 |  |  |  |  | 90 |  |  |  |  | 95 |  |
| Ile | Asn | Thr | Leu | Asn | Gly | Leu | Arg | Leu | Gln | Thr | Lys | Thr | Ile | Lys | Val |
|  |  |  | 100 |  |  |  |  |  | 105 |  |  |  | 110 |  |  |
| Ser | Tyr | Ala | Arg | Pro | Ser | Ser | Ala | Ser | Ile | Arg | Asp | Ala | Asn | Leu | Tyr |
|  |  | 115 |  |  |  |  | 120 |  |  |  |  | 125 |  |  |  |
| Val | Ser | Gly | Leu | Pro | Lys | Thr | Met | Thr | Gln | Lys | Glu | Leu | Glu | Gln | Leu |
|  | 130 |  |  |  |  | 135 |  |  |  |  | 140 |  |  |  |  |
| Phe | Ser | Gln | Tyr | Gly | Arg | Ile | Ile | Thr | Ser | Arg | Ile | Leu | Val | Asp | Gln |
| 145 |  |  |  |  | 150 |  |  |  |  | 155 |  |  |  |  | 160 |
| Val | Thr | Gly | Ile | Ser | Arg | Gly | Val | Gly | Phe | Ile | Arg | Phe | Asp | Lys | Arg |
|  |  |  |  | 165 |  |  |  |  | 170 |  |  |  |  | 175 |  |
| Ile | Glu | Ala | Glu | Glu | Ala | Ile | Lys | Gly | Leu | Asn | Gly | Gln | Lys | Pro | Pro |
|  |  |  | 180 |  |  |  |  |  | 185 |  |  |  | 190 |  |  |
| Gly | Ala | Thr | Glu | Pro | Ile | Thr | Val | Lys | Phe | Ala | Asn | Asn | Pro | Ser | Gln |
|  |  | 195 |  |  |  |  | 200 |  |  |  |  | 205 |  |  |  |
| Lys | Thr | Asn | Gln | Ala | Ile | Leu | Ser | Gln | Leu | Tyr | Gln | Ser | Pro | Asn | Arg |
|  | 210 |  |  |  |  | 215 |  |  |  |  | 220 |  |  |  |  |
| Arg | Tyr | Pro | Gly | Pro | Leu | Ala | Gln | Gln | Ala | Gln | Arg | Phe | Arg | Leu | Asp |
| 225 |  |  |  |  | 230 |  |  |  |  | 235 |  |  |  |  | 240 |
| Asn | Leu | Leu | Asn | Met | Ala | Tyr | Gly | Val | Lys | Arg | Phe | Ser | Pro | Met | Thr |
|  |  |  |  | 245 |  |  |  |  | 250 |  |  |  |  | 255 |  |
| Ile | Asp | Gly | Met | Thr | Ser | Leu | Ala | Gly | Ile | Asn | Ile | Pro | Gly | His | Pro |
|  |  |  | 260 |  |  |  |  |  | 265 |  |  |  | 270 |  |  |
| Gly | Thr | Gly | Trp | Cys | Ile | Phe | Val | Tyr | Asn | Leu | Ala | Pro | Asp | Ala | Asp |
|  |  | 275 |  |  |  |  | 280 |  |  |  |  | 285 |  |  |  |
| Glu | Ser | Ile | Leu | Trp | Gln | Met | Phe | Gly | Pro | Phe | Gly | Ala | Val | Thr | Asn |
|  | 290 |  |  |  |  | 295 |  |  |  |  | 300 |  |  |  |  |
| Val | Lys | Val | Ile | Arg | Asp | Phe | Asn | Thr | Asn | Lys | Cys | Lys | Gly | Phe | Gly |
| 305 |  |  |  |  | 310 |  |  |  |  | 315 |  |  |  |  | 320 |
| Phe | Val | Thr | Met | Thr | Asn | Tyr | Asp | Glu | Ala | Ala | Met | Ala | Ile | Arg | Ser |
|  |  |  |  | 325 |  |  |  |  | 330 |  |  |  |  | 335 |  |
| Leu | Asn | Gly | Tyr | Arg | Leu | Gly | Asp | Arg | Val | Leu | Gln | Val | Ser | Phe | Lys |
|  |  |  | 340 |  |  |  |  |  | 345 |  |  |  | 350 |  |  |
| Thr | Asn | Lys | Thr | His | Lys | Ala |  |  |  |  |  |  |  |  |  |
|  |  |  | 355 |  |  |  |  |  |  |  |  |  |  |  |  |

( 2 ) INFORMATION FOR SEQ ID NO:3:

( i ) SEQUENCE CHARACTERISTICS:
        ( A ) LENGTH: 444 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:3:

| Met | Val | Glu | Gly | Gln | Thr | Ala | Val | Gln | Gln | Gln | Gln | Gln | Pro | Ser |
|---|---|---|---|---|---|---|---|---|---|---|---|---|---|---|
| 1 |  |  |  | 5 |  |  |  |  | 10 |  |  |  |  | 15 |
| Gly | Ala | Gly | Gly | Ala | Ser | Gly | Val | Gly | Ser | Thr | Thr | Gly | Ser | Ala | Gly |
|  |  |  | 20 |  |  |  |  | 25 |  |  |  | 30 |  |  |  |
| Gly | Pro | Ala | Thr | Ala | Asn | Asn | Val | Thr | Asn | Ser | Gln | Ala | Gln | Thr | Asn |
|  |  | 35 |  |  |  |  | 40 |  |  |  |  | 45 |  |  |  |
| Gly | Gly | Thr | Thr | Ala | Thr | Thr | Thr | Ala | Ala | Ala | Gly | Ala | Gly | Ser | Thr |
|  | 50 |  |  |  |  | 55 |  |  |  |  | 60 |  |  |  |  |

```
Thr  Asn  Ala  Ala  Val  Gly  Gln  Ala  Thr  Ala  Asn  Ala  Ala  Ser  Asn
65             70                  75                       80

Asn  Asn  Asn  Asn  Asn  Asn  Thr  Asn  Asn  Asn  Asn  Asn  Asn  Asn  Ala
                85                  90                       95

Thr  Ala  Asn  Asn  Asn  Asn  Asn  Asn  Glu  Pro  Asp  Pro  Lys  Thr  Asn  Leu
               100                 105                      110

Ile  Val  Asn  Tyr  Leu  Pro  Gln  Thr  Met  Ser  Gln  Asp  Glu  Ile  Arg  Ser
               115                 120                      125

Leu  Phe  Val  Ser  Phe  Gly  Glu  Val  Glu  Ser  Cys  Lys  Leu  Ile  Arg  Asp
     130                      135                 140

Lys  Val  Thr  Gly  Gln  Ser  Leu  Gly  Tyr  Gly  Phe  Val  Xaa  Tyr  Val  Lys
145                      150                 155                           160

Gln  Glu  Asp  Ala  Glu  Lys  Ala  Ile  Asn  Ala  Leu  Asn  Gly  Leu  Arg  Leu
                165                 170                      175

Gln  Asn  Lys  Thr  Ile  Lys  Val  Ser  Ile  Ala  Arg  Pro  Ser  Ser  Glu  Ser
               180                 185                      190

Ile  Lys  Gly  Ala  Asn  Leu  Tyr  Val  Ser  Gly  Leu  Pro  Lys  Asn  Met  Thr
          195                 200                 205

Gln  Ser  Asp  Leu  Glu  Ser  Leu  Phe  Ser  Pro  Tyr  Gly  Lys  Ile  Ile  Thr
     210                      215                 220

Ser  Arg  Ile  Leu  Cys  Asp  Asn  Ile  Thr  Asp  Glu  His  Ala  Ala  Gly  Leu
225                      230                 235                           240

Ser  Lys  Gly  Val  Gly  Phe  Ile  Arg  Phe  Asp  Gln  Arg  Phe  Glu  Ala  Asp
                245                 250                      255

Arg  Ala  Ile  Lys  Glu  Leu  Asn  Gly  Thr  Thr  Pro  Lys  Asn  Ser  Thr  Glu
               260                 265                      270

Pro  Ile  Thr  Val  Lys  Phe  Ala  Asn  Asn  Pro  Ser  Ser  Asn  Lys  Asn  Ser
          275                 280                 285

Met  Gln  Pro  Leu  Ala  Ala  Tyr  Ile  Ala  Pro  Gln  Asn  Thr  Arg  Gly  Gly
     290                      295                 300

Arg  Ala  Phe  Pro  Ala  Asn  Ala  Ala  Ala  Gly  Ala  Ala  Ala  Ala  Ala  Ala
305                      310                 315                           320

Ala  Ala  Ala  Ile  His  Pro  Asn  Ala  Gly  Arg  Tyr  Ser  Ser  Val  Ile  Ser
               325                 330                      335

Arg  Tyr  Ser  Pro  Leu  Thr  Ser  Asp  Leu  Ile  Thr  Asn  Gly  Met  Ile  Gln
               340                 345                      350

Gly  Asn  Thr  Ile  Ala  Ser  Ser  Gly  Trp  Cys  Ile  Phe  Val  Tyr  Asn  Leu
          355                 360                 365

Ala  Pro  Glu  Thr  Glu  Glu  Asn  Val  Leu  Trp  Gln  Leu  Phe  Gly  Pro  Phe
     370                      375                 380

Gly  Ala  Val  Gln  Ser  Val  Lys  Val  Ile  Arg  Asp  Leu  Gln  Ser  Asn  Lys
385                      390                 395                           400

Cys  Lys  Gly  Phe  Gly  Phe  Val  Thr  Met  Thr  Asn  Tyr  Glu  Glu  Ala  Val
               405                 410                      415

Leu  Ala  Ile  Gln  Ser  Leu  Asn  Gly  Tyr  Thr  Leu  Gly  Asn  Arg  Val  Leu
               420                 425                      430

Gln  Val  Ser  Phe  Lys  Thr  Asn  Lys  Asn  Lys  Gln  Thr
          435                 440
```

( 2 ) INFORMATION FOR SEQ ID NO:4:

( i ) SEQUENCE CHARACTERISTICS:
        ( A ) LENGTH: 76 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:4:

| | | | | | | | | | | | | | | |
|---|---|---|---|---|---|---|---|---|---|---|---|---|---|---|
| Val | Ile | His | Ile | Arg | Lys | Leu | Pro | Ile | Asp | Val | Thr | Glu | Gly | Glu | Val |
| 1 | | | | 5 | | | | | 10 | | | | | 15 |
| Ile | Ser | Leu | Gly | Leu | Pro | Phe | Gly | Lys | Val | Thr | Asn | Leu | Leu | Met | Leu |
| | | | 20 | | | | | 25 | | | | | 30 | | |
| Lys | Gly | Lys | Asn | Gln | Ala | Phe | Ile | Glu | Met | Asn | Thr | Glu | Glu | Ala | Ala |
| | | 35 | | | | | 40 | | | | | 45 | | | |
| Asn | Thr | Met | Val | Asn | Tyr | Tyr | Thr | Ser | Val | Thr | Pro | Val | Leu | Arg | Gly |
| | | 50 | | | | 55 | | | | | 60 | | | | |
| Gln | Pro | Ile | Tyr | Ile | Gln | Phe | Ser | Asn | His | Lys | Glu | | | | |
| 65 | | | | | 70 | | | | | 75 | | | | | |

( 2 ) INFORMATION FOR SEQ ID NO:5:

( i ) SEQUENCE CHARACTERISTICS:
( A ) LENGTH: 78 amino acids
( B ) TYPE: amino acid
( D ) TOPOLOGY: unknown ( i i ) MOLECULE TYPE: peptide ( x i ) SEQUENCE DESCRIPTION: SEQ ID NO:5:

| | | | | | | | | | | | | | | | |
|---|---|---|---|---|---|---|---|---|---|---|---|---|---|---|---|
| Arg | Ile | Ile | Val | Glu | Asn | Leu | Phe | Tyr | Pro | Val | Thr | Leu | Asp | Val | Leu |
| 1 | | | | 5 | | | | | 10 | | | | | 15 | |
| Met | Gln | Ile | Phe | Ser | Lys | Phe | Gly | Thr | Val | Leu | Lys | Ile | Ile | Thr | Phe |
| | | | 20 | | | | | 25 | | | | | 30 | | |
| Thr | Lys | Asn | Asn | Gln | Phe | Gln | Ala | Leu | Leu | Gln | Tyr | Ala | Asp | Pro | Val |
| | | 35 | | | | | 40 | | | | | 45 | | | |
| Ser | Ala | Gln | His | Ala | Lys | Leu | Ser | Leu | Asp | Gly | Gln | Asn | Ile | Tyr | Asn |
| | | 50 | | | | 55 | | | | | 60 | | | | |
| Ala | Cys | Cys | Thr | Leu | Arg | Ile | Asp | Phe | Ser | Lys | Leu | Thr | Ser | | |
| 65 | | | | | 70 | | | | | 75 | | | | | |

( 2 ) INFORMATION FOR SEQ ID NO:6:

( i ) SEQUENCE CHARACTERISTICS:
( A ) LENGTH: 76 amino acids
( B ) TYPE: amino acid
( D ) TOPOLOGY: unknown ( i i ) MOLECULE TYPE: peptide ( x i ) SEQUENCE DESCRIPTION: SEQ ID NO:6:

| | | | | | | | | | | | | | | | |
|---|---|---|---|---|---|---|---|---|---|---|---|---|---|---|---|
| Val | Leu | Leu | Val | Ser | Asn | Leu | Asn | Pro | Glu | Arg | Val | Thr | Pro | Gln | Ser |
| 1 | | | | 5 | | | | | 10 | | | | | 15 | |
| Leu | Phe | Ile | Leu | Phe | Gly | Val | Tyr | Gly | Asp | Val | Gln | Arg | Val | Lys | Ile |
| | | | 20 | | | | | 25 | | | | | 30 | | |
| Leu | Phe | Asn | Lys | Lys | Glu | Asn | Ala | Leu | Val | Gln | Met | Ala | Asp | Gly | Asn |
| | | 35 | | | | | 40 | | | | | 45 | | | |
| Gln | Ala | Gln | Leu | Ala | Met | Ser | His | Leu | Asn | Gly | His | Lys | Leu | His | Gly |
| | | 50 | | | | 55 | | | | | 60 | | | | |
| Lys | Pro | Ile | Arg | Ile | Thr | Leu | Ser | Lys | His | Gln | Asn | | | | |
| 65 | | | | | 70 | | | | | 75 | | | | | |

( 2 ) INFORMATION FOR SEQ ID NO:7:

( i ) SEQUENCE CHARACTERISTICS:
( A ) LENGTH: 76 amino acids
( B ) TYPE: amino acid
( D ) TOPOLOGY: unknown ( i i ) MOLECULE TYPE: peptide ( x i ) SEQUENCE DESCRIPTION: SEQ ID NO:7:

| Val | Val | His | Ile | Arg | Gly | Leu | Ile | Asp | Gly | Val | Val | Glu | Ala | Asp | Leu |
|---|---|---|---|---|---|---|---|---|---|---|---|---|---|---|---|
| 1 | | | | 5 | | | | | 10 | | | | | 15 | |

| Val | Glu | Ala | Leu | Gln | Glu | Phe | Gly | Pro | Ile | Ser | Tyr | Val | Val | Val | Met |
|---|---|---|---|---|---|---|---|---|---|---|---|---|---|---|---|
| | | | 20 | | | | | 25 | | | | | 30 | | |

| Pro | Lys | Lys | Arg | Gln | Ala | Leu | Val | Glu | Phe | Glu | Asp | Val | Leu | Gly | Ala |
|---|---|---|---|---|---|---|---|---|---|---|---|---|---|---|---|
| | | 35 | | | | | 40 | | | | | 45 | | | |

| Cys | Asn | Ala | Val | Asn | Tyr | Ala | Ala | Asp | Asn | Gln | Ile | Tyr | Ile | Ala | Gly |
|---|---|---|---|---|---|---|---|---|---|---|---|---|---|---|---|
| | 50 | | | | | 55 | | | | | 60 | | | | |

| His | Pro | Ala | Phe | Val | Asn | Tyr | Ser | Thr | Ser | Gln | Lys |
|---|---|---|---|---|---|---|---|---|---|---|---|
| 65 | | | | | 70 | | | | | 75 | |

( 2 ) INFORMATION FOR SEQ ID NO:8:

( i ) SEQUENCE CHARACTERISTICS:
        ( A ) LENGTH: 77 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

| Leu | Phe | Thr | Ile | Leu | Asn | Pro | Ile | Tyr | Ser | Ile | Thr | Thr | Asp | Val | Leu |
|---|---|---|---|---|---|---|---|---|---|---|---|---|---|---|---|
| 1 | | | | 5 | | | | | 10 | | | | | 15 | |

| Tyr | Thr | Ile | Cys | Asn | Pro | Cys | Gly | Pro | Val | Gln | Arg | Ile | Val | Ile | Phe |
|---|---|---|---|---|---|---|---|---|---|---|---|---|---|---|---|
| | | | 20 | | | | | 25 | | | | | 30 | | |

| Arg | Lys | Asn | Gly | Val | Gln | Ala | Met | Val | Glu | Phe | Asp | Ser | Val | Gln | Ser |
|---|---|---|---|---|---|---|---|---|---|---|---|---|---|---|---|
| | | 35 | | | | | 40 | | | | | 45 | | | |

| Ala | Gln | Arg | Ala | Lys | Ala | Ser | Leu | Asn | Gly | Ala | Asp | Ile | Tyr | Ser | Gly |
|---|---|---|---|---|---|---|---|---|---|---|---|---|---|---|---|
| | 50 | | | | | 55 | | | | | 60 | | | | |

| Cys | Cys | Thr | Leu | Lys | Ile | Glu | Tyr | Ala | Lys | Pro | Thr | Arg |
|---|---|---|---|---|---|---|---|---|---|---|---|---|
| 65 | | | | | 70 | | | | | 75 | | |

( 2 ) INFORMATION FOR SEQ ID NO:9:

( i ) SEQUENCE CHARACTERISTICS:
        ( A ) LENGTH: 76 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:9:

| Val | Leu | Met | Val | Tyr | Gly | Leu | Asp | Gln | Ser | Lys | Met | Asn | Gly | Asp | Arg |
|---|---|---|---|---|---|---|---|---|---|---|---|---|---|---|---|
| 1 | | | | 5 | | | | | 10 | | | | | 15 | |

| Val | Phe | Asn | Val | Phe | Cys | Leu | Tyr | Gly | Asn | Val | Glu | Lys | Val | Lys | Phe |
|---|---|---|---|---|---|---|---|---|---|---|---|---|---|---|---|
| | | | 20 | | | | | 25 | | | | | 30 | | |

| Met | Lys | Ser | Lys | Pro | Gly | Ala | Ala | Met | Val | Glu | Met | Ala | Asp | Gly | Tyr |
|---|---|---|---|---|---|---|---|---|---|---|---|---|---|---|---|
| | | 35 | | | | | 40 | | | | | 45 | | | |

| Ala | Val | Asp | Arg | Ala | Ile | Thr | His | Leu | Asn | Asn | Asn | Phe | Met | Phe | Gly |
|---|---|---|---|---|---|---|---|---|---|---|---|---|---|---|---|
| | 50 | | | | | 55 | | | | | 60 | | | | |

| Gln | Lys | Leu | Asn | Val | Cys | Val | Ser | Lys | Gln | Pro | Ala |
|---|---|---|---|---|---|---|---|---|---|---|---|
| 65 | | | | | 70 | | | | | 75 | |

( 2 ) INFORMATION FOR SEQ ID NO:10:

( i ) SEQUENCE CHARACTERISTICS:
        ( A ) LENGTH: 80 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:10:

```
Asn Leu Ile Val Asn Xaa Leu Pro Gln Asp Met Thr Asp Arg Glu Leu
1               5                   10                  15

Tyr Ala Leu Phe Arg Ala Ile Gly Pro Ile Asn Thr Cys Arg Ile Met
            20                  25                  30

Arg Asp Tyr Lys Thr Gly Tyr Ser Phe Gly Tyr Ala Phe Val Asp Phe
            35              40                  45

Thr Ser Glu Met Asp Ser Gln Arg Ala Ile Lys Val Leu Asn Gly Ile
        50              55                  60

Thr Val Arg Asn Lys Leu Lys Val Ser Tyr Ala Arg Pro Gly Gly
65                  70                  75                  80
```

(2) INFORMATION FOR SEQ ID NO:11:

(i) SEQUENCE CHARACTERISTICS:
      (A) LENGTH: 82 amino acids
      (B) TYPE: amino acid
      (D) TOPOLOGY: unknown (ii) MOLECULE TYPE: peptide (xi) SEQUENCE DESCRIPTION: SEQ ID NO:11:

```
Asn Leu Tyr Val Thr Asn Leu Pro Arg Thr Ile Thr Asp Asp Gln Leu
1               5                   10                  15

Asp Thr Ile Phe Gly Lys Tyr Gly Ser Ile Val Gln Lys Asn Ile Leu
            20                  25                  30

Arg Asp Lys Leu Thr Gly Arg Pro Arg Gly Val Ala Phe Val Arg Tyr
            35              40                  45

Asn Lys Arg Glu Glu Ala Gln Glu Ala Ile Ser Ala Leu Asn Asn Val
        50              55                  60

Ile Pro Glu Gly Gly Ser Gln Pro Leu Ser Val Arg Leu Ala Glu Glu
65                  70                  75                  80

His Gly
```

(2) INFORMATION FOR SEQ ID NO:12:

(i) SEQUENCE CHARACTERISTICS:
      (A) LENGTH: 75 amino acids
      (B) TYPE: amino acid
      (D) TOPOLOGY: unknown (ii) MOLECULE TYPE: peptide (xi) SEQUENCE DESCRIPTION: SEQ ID NO:12:

```
Lys Val Tyr Val Gly Asn Leu Gly Ser Ser Ala Ser Lys His Glu Ile
1               5                   10                  15

Glu Gly Ala Phe Ala Lys Tyr Gly Pro Leu Arg Asn Val Trp Val Ala
            20                  25                  30

Arg Asn Pro Pro Gly Phe Ala Phe Val Glu Phe Glu Asp Arg Arg Asp
            35              40                  45

Ala Glu Asp Ala Thr Arg Ala Leu Asp Gly Thr Arg Cys Cys Gly Thr
        50              55                  60

Arg Ile Arg Val Glu Met Ser Ser Gly Arg Ser
65                  70                  75
```

(2) INFORMATION FOR SEQ ID NO:13:

(i) SEQUENCE CHARACTERISTICS:
      (A) LENGTH: 81 amino acids
      (B) TYPE: amino acid
      (D) TOPOLOGY: unknown (ii) MOLECULE TYPE: peptide ( x i ) SEQUENCE DESCRIPTION: SEQ ID NO:13:

| Ile | Ala | Phe | Val | Gly | Asn | Leu | Pro | Gln | Gly | Leu | Val | Gln | Gly | Asp | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ile | Lys | Ile | Phe | Gln | Asp | Phe | Glu | Val | Lys | Tyr | Val | Arg | Leu | Val | Lys |
|-----|-----|-----|-----|-----|-----|-----|-----|-----|-----|-----|-----|-----|-----|-----|-----|
|     |     |     | 20  |     |     |     | 25  |     |     |     |     |     | 30  |     |     |

| Asp | Arg | Glu | Thr | Asp | Gln | Phe | Lys | Gly | Phe | Cys | Tyr | Val | Glu | Phe | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Thr | Leu | Asp | Asn | Leu | Glu | Arg | Ala | Leu | Glu | Cys | Asp | Gly | Arg | Ile | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Leu | Asp | Asp | Leu | Ser | Ala | Pro | Leu | Arg | Ile | Asp | Ile | Ala | Asp | Arg | Arg |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

Lys ( 2 ) INFORMATION FOR SEQ ID NO:14:

( i ) SEQUENCE CHARACTERISTICS:
    ( A ) LENGTH: 93 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:14:

| Asn | Leu | Ile | Val | Asn | Tyr | Leu | Pro | Gln | Thr | Met | Thr | Glu | Asp | Glu | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Ser | Leu | Phe | Ser | Ser | Val | Gly | Glu | Ile | Glu | Ser | Val | Lys | Leu | Ile |
|-----|-----|-----|-----|-----|-----|-----|-----|-----|-----|-----|-----|-----|-----|-----|-----|
|     |     |     | 20  |     |     |     | 25  |     |     |     |     |     | 30  |     |     |

| Arg | Asp | Lys | Ser | Gln | Val | Tyr | Ile | Asp | Pro | Leu | Asn | Pro | Gln | Ala | Pro |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ser | Lys | Gly | Gln | Ser | Leu | Gly | Tyr | Gly | Phe | Val | Asn | Tyr | Val | Arg | Pro |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gln | Asp | Ala | Glu | Gln | Ala | Val | Asn | Val | Leu | Asn | Gly | Leu | Arg | Leu | Gln |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Asn | Lys | Thr | Ile | Lys | Val | Ser | Phe | Ala | Arg | Pro | Ser | Ser |
|-----|-----|-----|-----|-----|-----|-----|-----|-----|-----|-----|-----|-----|
|     |     |     |     | 85  |     |     |     |     | 90  |     |     |     |

( 2 ) INFORMATION FOR SEQ ID NO:15:

( i ) SEQUENCE CHARACTERISTICS:
    ( A ) LENGTH: 80 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:15:

| Asn | Leu | Ile | Val | Asn | Tyr | Leu | Pro | Gln | Thr | Met | Ser | Gln | Asp | Glu | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Ser | Leu | Phe | Val | Ser | Phe | Gly | Glu | Val | Glu | Ser | Cys | Lys | Leu | Ile |
|-----|-----|-----|-----|-----|-----|-----|-----|-----|-----|-----|-----|-----|-----|-----|-----|
|     |     |     | 20  |     |     |     | 25  |     |     |     |     |     | 30  |     |     |

| Arg | Asp | Lys | Val | Thr | Gly | Gln | Ser | Leu | Gly | Tyr | Gly | Phe | Val | Asn | Tyr |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Val | Lys | Gln | Glu | Asp | Ala | Glu | Lys | Ala | Ile | Asn | Ala | Leu | Asn | Gly | Leu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Arg | Leu | Gln | Asn | Lys | Thr | Ile | Lys | Val | Ser | Ile | Ala | Arg | Pro | Ser | Ser |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

( 2 ) INFORMATION FOR SEQ ID NO:16:

( i ) SEQUENCE CHARACTERISTICS:
    ( A ) LENGTH: 80 amino acids
    ( B ) TYPE: amino acid (D) TOPOLOGY: unknown (ii) MOLECULE TYPE: peptide (xi) SEQUENCE DESCRIPTION: SEQ ID NO:16:

```
Asn Leu Ile Val Asn Tyr Leu Pro Gln Asn Met Thr Gln Glu Glu Leu
 1               5                  10                  15

Lys Ser Leu Phe Gly Ser Ile Gly Glu Ile Glu Ser Cys Lys Leu Val
                20                  25                  30

Arg Asp Lys Ile Thr Gly Gln Ser Leu Gly Tyr Gly Phe Val Asn Tyr
            35                  40                  45

Ile Asp Pro Lys Asp Ala Glu Lys Ala Ile Asn Thr Leu Asn Gly Leu
        50                  55                  60

Arg Leu Gln Thr Lys Thr Ile Lys Val Ser Tyr Ala Arg Pro Ser Ser
 65                 70                  75                  80
```

(2) INFORMATION FOR SEQ ID NO:17:

(i) SEQUENCE CHARACTERISTICS:
        (A) LENGTH: 83 amino acids
        (B) TYPE: amino acid
        (D) TOPOLOGY: unknown (ii) MOLECULE TYPE: peptide (xi) SEQUENCE DESCRIPTION: SEQ ID NO:17:

```
Asn Leu Tyr Val Ser Gly Leu Pro Lys Thr Met Thr Gln Gln Glu Leu
 1               5                  10                  15

Glu Ala Ile Phe Ala Pro Phe Gly Ala Ile Ile Thr Ser Arg Ile Leu
                20                  25                  30

Gln Asn Ala Gly Asn Asp Thr Gln Thr Lys Gly Val Gly Phe Ile Arg
            35                  40                  45

Phe Asp Lys Arg Glu Glu Ala Thr Arg Ala Ile Ile Ala Leu Asn Gly
        50                  55                  60

Thr Thr Pro Ser Ser Cys Thr Asp Pro Ile Val Val Lys Phe Ser Asn
 65                 70                  75                  80

Thr Pro Gly
```

(2) INFORMATION FOR SEQ ID NO:18:

(i) SEQUENCE CHARACTERISTICS:
        (A) LENGTH: 87 amino acids
        (B) TYPE: amino acid
        (D) TOPOLOGY: unknown (ii) MOLECULE TYPE: peptide (xi) SEQUENCE DESCRIPTION: SEQ ID NO:18:

```
Asn Leu Tyr Val Ser Gly Leu Pro Lys Asn Met Thr Gln Ser Asp Leu
 1               5                  10                  15

Glu Ser Leu Phe Ser Pro Tyr Gly Lys Ile Ile Thr Ser Arg Ile Leu
                20                  25                  30

Cys Asp Asn Ile Thr Asp Glu Asn Ala Ala Gly Leu Ser Lys Gly Val
            35                  40                  45

Gly Phe Ile Arg Phe Asp Gln Arg Phe Glu Ala Asp Arg Ala Ile Lys
        50                  55                  60

Glu Leu Asn Gly Thr Thr Pro Lys Asn Ser Thr Glu Pro Ile Thr Val
 65                 70                  75                  80

Lys Phe Ala Asn Asn Pro Ser
                85
```

(2) INFORMATION FOR SEQ ID NO:19:

( i ) SEQUENCE CHARACTERISTICS:
( A ) LENGTH: 82 amino acids
( B ) TYPE: amino acid
( D ) TOPOLOGY: unknown ( i i ) MOLECULE TYPE: peptide ( x i ) SEQUENCE DESCRIPTION: SEQ ID NO:19:

| Asn | Leu | Tyr | Val | Ser | Gly | Leu | Pro | Lys | Thr | Met | Thr | Gln | Lys | Glu | Leu |
|---|---|---|---|---|---|---|---|---|---|---|---|---|---|---|---|
| 1 | | | | 5 | | | | | 10 | | | | | 15 | |
| Glu | Gln | Leu | Phe | Ser | Gln | Tyr | Gly | Arg | Ile | Ile | Thr | Ser | Arg | Ile | Leu |
| | | | 20 | | | | | 25 | | | | | 30 | | |
| Val | Asp | Gln | Val | Thr | Gly | Ile | Ser | Arg | Gly | Val | Gly | Phe | Ile | Arg | Phe |
| | | 35 | | | | | 40 | | | | | 45 | | | |
| Asp | Lys | Arg | Ile | Glu | Ala | Glu | Ala | Ile | Lys | Gly | Leu | Asn | Gly | Gln |
| 50 | | | | | 55 | | | | | 60 | | | | |
| Lys | Pro | Pro | Gly | Ala | Thr | Glu | Pro | Ile | Thr | Val | Lys | Phe | Ala | Asn | Asn |
| 65 | | | | | 70 | | | | | 75 | | | | | 80 |
| Pro | Ser | | | | | | | | | | | | | | |

( 2 ) INFORMATION FOR SEQ ID NO:20:

( i ) SEQUENCE CHARACTERISTICS:
( A ) LENGTH: 80 amino acids
( B ) TYPE: amino acid
( D ) TOPOLOGY: unknown ( i i ) MOLECULE TYPE: peptide ( x i ) SEQUENCE DESCRIPTION: SEQ ID NO:20:

| Pro | Ile | Phe | Ile | Tyr | Asn | Leu | Ala | Pro | Glu | Thr | Glu | Glu | Ala | Ala | Leu |
|---|---|---|---|---|---|---|---|---|---|---|---|---|---|---|---|
| 1 | | | | 5 | | | | | 10 | | | | | 15 | |
| Trp | Gln | Leu | Phe | Gly | Pro | Phe | Gly | Ala | Val | Gln | Ser | Val | Lys | Ile | Val |
| | | | 20 | | | | | 25 | | | | | 30 | | |
| Lys | Asp | Pro | Thr | Thr | Asn | Gln | Cys | Lys | Gly | Tyr | Gly | Phe | Val | Ser | Met |
| | | 35 | | | | | 40 | | | | | 45 | | | |
| Thr | Asn | Tyr | Asp | Glu | Ala | Ala | Met | Ala | Ile | Arg | Ala | Leu | Asn | Gly | Tyr |
| | 50 | | | | | 55 | | | | | 60 | | | | |
| Thr | Met | Gly | Asn | Arg | Val | Leu | Gln | Val | Ser | Phe | Lys | Thr | Asn | Lys | Ala |
| 65 | | | | | 70 | | | | | 75 | | | | | 80 |

( 2 ) INFORMATION FOR SEQ ID NO:21:

( i ) SEQUENCE CHARACTERISTICS:
( A ) LENGTH: 80 amino acids
( B ) TYPE: amino acid
( D ) TOPOLOGY: unknown ( i i ) MOLECULE TYPE: peptide ( x i ) SEQUENCE DESCRIPTION: SEQ ID NO:21:

| Cys | Ile | Phe | Val | Tyr | Asn | Leu | Ala | Pro | Glu | Thr | Glu | Glu | Asn | Val | Leu |
|---|---|---|---|---|---|---|---|---|---|---|---|---|---|---|---|
| 1 | | | | 5 | | | | | 10 | | | | | 15 | |
| Trp | Gln | Leu | Phe | Gly | Pro | Phe | Gly | Ala | Val | Gln | Ser | Val | Lys | Val | Ile |
| | | | 20 | | | | | 25 | | | | | 30 | | |
| Arg | Asp | Leu | Gln | Ser | Asn | Lys | Cys | Lys | Gly | Phe | Gly | Phe | Val | Thr | Met |
| | | 35 | | | | | 40 | | | | | 45 | | | |
| Thr | Asn | Tyr | Glu | Glu | Ala | Val | Leu | Ala | Ile | Gln | Ser | Leu | Asn | Gly | Tyr |
| | 50 | | | | | 55 | | | | | 60 | | | | |
| Thr | Leu | Gly | Asn | Arg | Val | Leu | Gln | Val | Ser | Phe | Lys | Thr | Asn | Lys | Asn |
| 65 | | | | | 70 | | | | | 75 | | | | | 80 |

(2) INFORMATION FOR SEQ ID NO:22:

(i) SEQUENCE CHARACTERISTICS:
        (A) LENGTH: 80 amino acids
        (B) TYPE: amino acid
        (D) TOPOLOGY: unknown (ii) MOLECULE TYPE: peptide (xi) SEQUENCE DESCRIPTION: SEQ ID NO:22:

```
Cys Ile Phe Val Tyr Asn Leu Ala Pro Asp Ala Asp Glu Ser Ile Leu
 1               5                  10                  15
Trp Gln Met Phe Gly Pro Phe Gly Ala Val Thr Asn Val Lys Val Ile
            20                  25                  30
Arg Asp Phe Asn Thr Asn Lys Cys Lys Gly Phe Gly Phe Val Thr Met
        35                  40                  45
Thr Asn Tyr Asp Glu Ala Ala Met Ala Ile Arg Ser Leu Asn Gly Tyr
    50                  55                  60
Arg Leu Gly Asp Arg Val Leu Gln Val Ser Phe Lys Thr Asn Lys Thr
65                  70                  75                  80
```

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:23:

UCCAGUAACC CCACCUCCUC UUUUU                          25

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:24:

UCAGUUAAAC GUGUAAACCU UUUAA                          25

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:25:

UCAUAGCACC ACCUCACCCU UUUUA                          25

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: RNA (genomic)

( x i ) SEQUENCE DESCRIPTION: SEQ ID NO:26:

UCAUAGCACC ACCUCACCCU UUUUA                25

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:27:

GGGCUAGGCU UAUCCUCCUU UCC                  23

( 2 ) INFORMATION FOR SEQ ID NO:28:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:28:

AUCAUAAAUU CAGUGUCAUU UUUCU                25

( 2 ) INFORMATION FOR SEQ ID NO:29:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:29:

UUAUUUAUUU GCGUCUCCUU UAUUA                25

( 2 ) INFORMATION FOR SEQ ID NO:30:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:30:

AACUACCGGA GUACAGAUUU UUUUA                25

( 2 ) INFORMATION FOR SEQ ID NO:31:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:31:

UCAGUGGCAU CUCUUUCUUU ACUUU                25

( 2 ) INFORMATION FOR SEQ ID NO:32:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:32:

CACAACCCUA ACUUCAUUU GCUUU    25

( 2 ) INFORMATION FOR SEQ ID NO:33:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:33:

UGACCGAUAC ACAUUCUUUU AUUUA    25

( 2 ) INFORMATION FOR SEQ ID NO:34:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:34:

AUUGACUUCG UUAUUGUUUU UAUUG    25

( 2 ) INFORMATION FOR SEQ ID NO:35:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:35:

AGACGCAAUU AAUGAUUUGU UUUUA    25

( 2 ) INFORMATION FOR SEQ ID NO:36:

( i ) SEQUENCE CHARACTERISTICS:
    ( A ) LENGTH: 24 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:36:

UAGCUCGGAC AUUUAUUUUU AUUU    24

( 2 ) INFORMATION FOR SEQ ID NO:37:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:37:

UUAGGUUUCU UUUUAUUUGA GCAUA    25

( 2 ) INFORMATION FOR SEQ ID NO:38:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:38:

AUUUCUCAUU UAACGUCUCU CCUUU    25

( 2 ) INFORMATION FOR SEQ ID NO:39:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:39:

ACACCCUUUU UAGUUCCUGU AUUU    24

( 2 ) INFORMATION FOR SEQ ID NO:40:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:40:

CUAAUUUCCG AUAUUAAAGC UUAUUA    26

( 2 ) INFORMATION FOR SEQ ID NO:41:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:41:

AUGAUUUAGA UUUUCGCACA UUUCA    25

( 2 ) INFORMATION FOR SEQ ID NO:42:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:42:

UACUUUCGGU ACUAAAAUCG AUCAG    25

( 2 ) INFORMATION FOR SEQ ID NO:43:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: RNA (genomic)

( x i ) SEQUENCE DESCRIPTION: SEQ ID NO:43:

UCCUUUUUGU ACCACUCUCA GUUGU      25

( 2 ) INFORMATION FOR SEQ ID NO:44:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:44:

UUAUUUAUUU GCGUCUCCUU UAUUA      25

( 2 ) INFORMATION FOR SEQ ID NO:45:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:45:

UUAUUUAUUU GCGUCUCCUU UAUUA      25

( 2 ) INFORMATION FOR SEQ ID NO:46:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:46:

UUUGUUUUCG UGUAACGCAU AUACU      25

( 2 ) INFORMATION FOR SEQ ID NO:47:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:47:

UUUAGUUUAA UAGGGAUAAU ACUUA      25

( 2 ) INFORMATION FOR SEQ ID NO:48:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown (ii) MOLECULE TYPE: RNA (genomic)

(xi) SEQUENCE DESCRIPTION: SEQ ID NO:48:

UUUGUUUUCG UGUAACGCAU AUACU  25

(2) INFORMATION FOR SEQ ID NO:49:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: RNA (genomic)

(xi) SEQUENCE DESCRIPTION: SEQ ID NO:49:

UUGAUUUUCG CGCCCGCCGC CUUAG  25

(2) INFORMATION FOR SEQ ID NO:50:

(i) SEQUENCE CHARACTERISTICS:
        (A) LENGTH: 1467 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 95..1234

(xi) SEQUENCE DESCRIPTION: SEQ ID NO:50:

```
CCAATAGTAG TCATTTTAAA TATATATTCT GAAATCTTTG CAAATTTTAA CAGAAGAGTC        60

GAAGCTCTGC GAGACCCAAT ATTTGCCAAT AAGA ATG GTT ATG ATA ATT AGC           112
                                     Met Val Met Ile Ile Ser
                                      1               5

ACC ATG GAG CCT CAG GTG TCA AAT GGT CCG ACA TCC AAT ACA AGC AAT         160
Thr Met Glu Pro Gln Val Ser Asn Gly Pro Thr Ser Asn Thr Ser Asn
         10                  15                  20

GGA CCC TCC AGC AAC AAC AGA AAC TGT CCT TCT CCC ATG CAA ACA GGG         208
Gly Pro Ser Ser Asn Asn Arg Asn Cys Pro Ser Pro Met Gln Thr Gly
             25                  30                  35

GCA ACC ACA GAT GAC AGC AAA ACC AAC CTC ATC GTC AAC TAT TTA CCC         256
Ala Thr Thr Asp Asp Ser Lys Thr Asn Leu Ile Val Asn Tyr Leu Pro
 40                  45                  50

CAG AAT ATG ACC CAA GAA GAA TTC AGG AGT CTC TTC GGG AGC ATT GGT         304
Gln Asn Met Thr Gln Glu Glu Phe Arg Ser Leu Phe Gly Ser Ile Gly
 55                  60                  65                  70

GAA ATA GAA TCC TGC AAA CTT GTG AGA GAC AAA ATT ACA GGA CAG AGT         352
Glu Ile Glu Ser Cys Lys Leu Val Arg Asp Lys Ile Thr Gly Gln Ser
                 75                  80                  85

TTA GGG TAT GGA TTT GTT AAC TAT ATT GAT CCA AAG GAT GCA GAG AAA         400
Leu Gly Tyr Gly Phe Val Asn Tyr Ile Asp Pro Lys Asp Ala Glu Lys
             90                  95                 100

GCC ATC AAC ACT TTA AAT GGA CTC AGA CTC CAG ACC AAA ACC ATA AAG         448
Ala Ile Asn Thr Leu Asn Gly Leu Arg Leu Gln Thr Lys Thr Ile Lys
         105                 110                 115

GTC TCA TAT GCC CGT CCG AGC TCT GCC TCA ATC AGG GAT GCT AAC CTC         496
Val Ser Tyr Ala Arg Pro Ser Ser Ala Ser Ile Arg Asp Ala Asn Leu
 120                 125                 130

TAT GTT AGC GGC CTT CCC AAA ACC ATG ACC CAG AAG GAA CTG GAG CAA         544
Tyr Val Ser Gly Leu Pro Lys Thr Met Thr Gln Lys Glu Leu Glu Gln
135                 140                 145                 150

CTT TTC TCG CAA TAC GGC CGT ATC ATC ACC TCA CGA ATC CTG GTT GAT         592
Leu Phe Ser Gln Tyr Gly Arg Ile Ile Thr Ser Arg Ile Leu Val Asp
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 155 |     |     |     |     | 160 |     |     |     |     | 165 |     |      |
| CAA | GTC | ACA | GGA | GTG | TCC | AGA | GGG | GTG | GGA | TTC | ATC | CGC | TTT | GAT | AAG | 640  |
| Gln | Val | Thr | Gly | Val | Ser | Arg | Gly | Val | Gly | Phe | Ile | Arg | Phe | Asp | Lys |      |
|     |     |     | 170 |     |     |     |     | 175 |     |     |     |     | 180 |     |     |      |
| AGG | ATT | GAG | GCA | GAA | GAA | GCC | ATC | AAA | GGG | CTG | AAT | GGC | CAG | AAG | CCC | 688  |
| Arg | Ile | Glu | Ala | Glu | Glu | Ala | Ile | Lys | Gly | Leu | Asn | Gly | Gln | Lys | Pro |      |
|     |     | 185 |     |     |     |     | 190 |     |     |     |     | 195 |     |     |     |      |
| AGC | GGT | GCT | ACG | GAA | CCG | ATT | ACT | GTG | AAG | TTT | GCC | AAC | AAC | CCC | AGC | 736  |
| Ser | Gly | Ala | Thr | Glu | Pro | Ile | Thr | Val | Lys | Phe | Ala | Asn | Asn | Pro | Ser |      |
|     | 200 |     |     |     |     | 205 |     |     |     |     | 210 |     |     |     |     |      |
| CAG | AAG | TCC | AGC | CAG | GCC | CTG | CTC | TCC | CAG | CTC | TAC | CAG | TCC | CCT | AAC | 784  |
| Gln | Lys | Ser | Ser | Gln | Ala | Leu | Leu | Ser | Gln | Leu | Tyr | Gln | Ser | Pro | Asn |      |
| 215 |     |     |     |     | 220 |     |     |     |     | 225 |     |     |     |     | 230 |      |
| CGG | CGC | TAC | CCA | GGT | CCA | CTT | CAC | CAC | CAG | GCT | CAG | AGG | TTC | AGG | CTG | 832  |
| Arg | Arg | Tyr | Pro | Gly | Pro | Leu | His | His | Gln | Ala | Gln | Arg | Phe | Arg | Leu |      |
|     |     |     |     | 235 |     |     |     |     | 240 |     |     |     |     | 245 |     |      |
| GAC | AAT | TTG | CTT | AAT | ATG | GCC | TAT | GGC | GTA | AAG | AGA | CTG | ATG | TCT | GGA | 880  |
| Asp | Asn | Leu | Leu | Asn | Met | Ala | Tyr | Gly | Val | Lys | Arg | Leu | Met | Ser | Gly |      |
|     |     |     | 250 |     |     |     |     | 255 |     |     |     |     | 260 |     |     |      |
| CCA | GTC | CCC | CCT | TCT | GCT | TGT | TCC | CCC | AGG | TTC | TCC | CCA | ATT | ACC | ATT | 928  |
| Pro | Val | Pro | Pro | Ser | Ala | Cys | Ser | Pro | Arg | Phe | Ser | Pro | Ile | Thr | Ile |      |
|     |     | 265 |     |     |     |     | 270 |     |     |     |     | 275 |     |     |     |      |
| GAT | GGA | ATG | ACA | AGC | CTT | GTG | GGA | ATG | AAC | ATC | CCT | GGT | CAC | ACA | GGA | 976  |
| Asp | Gly | Met | Thr | Ser | Leu | Val | Gly | Met | Asn | Ile | Pro | Gly | His | Thr | Gly |      |
|     | 280 |     |     |     |     | 285 |     |     |     |     | 290 |     |     |     |     |      |
| ACT | GGG | TGG | TGC | ATC | TTT | GTC | TAC | AAC | CTG | TCC | CCC | GAT | TCC | GAT | GAG | 1024 |
| Thr | Gly | Trp | Cys | Ile | Phe | Val | Tyr | Asn | Leu | Ser | Pro | Asp | Ser | Asp | Glu |      |
| 295 |     |     |     |     | 300 |     |     |     |     | 305 |     |     |     |     | 310 |      |
| AGT | GTC | CTC | TGG | CAG | CTC | TTT | GGC | CCC | TTT | GGA | GCA | GTG | AAC | AAC | GTA | 1072 |
| Ser | Val | Leu | Trp | Gln | Leu | Phe | Gly | Pro | Phe | Gly | Ala | Val | Asn | Asn | Val |      |
|     |     |     | 315 |     |     |     |     | 320 |     |     |     |     | 325 |     |     |      |
| AAG | GTG | ATT | CGT | GAC | TTC | AAC | ACC | AAC | AAG | TGC | AAG | GGA | TTC | GGC | TTT | 1120 |
| Lys | Val | Ile | Arg | Asp | Phe | Asn | Thr | Asn | Lys | Cys | Lys | Gly | Phe | Gly | Phe |      |
|     |     |     | 330 |     |     |     |     | 335 |     |     |     |     | 340 |     |     |      |
| GTC | ACC | ATG | ACC | AAC | TAT | GAT | GAG | GCG | GCC | ATG | GCC | ATC | GCC | AGC | CTC | 1168 |
| Val | Thr | Met | Thr | Asn | Tyr | Asp | Glu | Ala | Ala | Met | Ala | Ile | Ala | Ser | Leu |      |
|     |     | 345 |     |     |     |     | 350 |     |     |     |     | 355 |     |     |     |      |
| AAC | GGG | TAC | CGC | CTG | GGA | GAC | AGA | GTG | TTG | CAA | GTT | TCC | TTT | AAA | ACC | 1216 |
| Asn | Gly | Tyr | Arg | Leu | Gly | Asp | Arg | Val | Leu | Gln | Val | Ser | Phe | Lys | Thr |      |
|     | 360 |     |     |     |     | 365 |     |     |     |     | 370 |     |     |     |     |      |
| AAC | AAA | GCC | CAC | AAG | TCC | TGAATTTCCC | ATTCTTACTT | ACTAAAATAT |     |     |     |     |     |     |     | 1264 |
| Asn | Lys | Ala | His | Lys | Ser |     |     |     |     |     |     |     |     |     |     |      |
| 375 |     |     |     |     | 380 |     |     |     |     |     |     |     |     |     |     |      |

```
ATATAGAAAT ATATACGAAC AAAACACACG CGCGCACACA CACATACACG AAAGAGAGAG     1324

AAACAAACTT TTCAAGGCTT ATATTCAACC ATGGACTTTA TAAGCCAGTG TTGCCTAGTA     1384

TTAAAACATT GGGTTATCCT GAGGTGTACC AGGAAAGGAT TATAATGCTT AGAAAAAAAA     1444

AAAGAAAAAA AAAAAACAAA AAA                                             1467
```

( 2 ) INFORMATION FOR SEQ ID NO:51:

( i ) SEQUENCE CHARACTERISTICS:
        ( A ) LENGTH: 380 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

| Met | Val | Met | Ile | Ile | Ser | Thr | Met | Glu | Pro | Gln | Val | Ser | Asn | Gly | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Thr | Ser | Asn | Thr | Ser | Asn | Gly | Pro | Ser | Ser | Asn | Asn | Arg | Asn | Cys | Pro |

-continued

```
                         20                          25                          30
    Ser  Pro  Met  Gln  Thr  Gly  Ala  Thr  Thr  Asp  Asp  Ser  Lys  Thr  Asn  Leu
              35                       40                       45

Ile  Val  Asn  Tyr  Leu  Pro  Gln  Asn  Met  Thr  Gln  Glu  Phe  Arg  Ser
              50                       55                       60

Leu  Phe  Gly  Ser  Ile  Gly  Glu  Ile  Glu  Ser  Cys  Lys  Leu  Val  Arg  Asp
    65                       70                       75                        80

Lys  Ile  Thr  Gly  Gln  Ser  Leu  Gly  Tyr  Gly  Phe  Val  Asn  Tyr  Ile  Asp
                        85                       90                       95

Pro  Lys  Asp  Ala  Glu  Lys  Ala  Ile  Asn  Thr  Leu  Asn  Gly  Leu  Arg  Leu
                   100                      105                     110

Gln  Thr  Lys  Thr  Ile  Lys  Val  Ser  Tyr  Ala  Arg  Pro  Ser  Ser  Ala  Ser
              115                      120                     125

Ile  Arg  Asp  Ala  Asn  Leu  Tyr  Val  Ser  Gly  Leu  Pro  Lys  Thr  Met  Thr
         130                      135                     140

Gln  Lys  Glu  Leu  Glu  Gln  Leu  Phe  Ser  Gln  Tyr  Gly  Arg  Ile  Ile  Thr
    145                      150                     155                      160

Ser  Arg  Ile  Leu  Val  Asp  Gln  Val  Thr  Gly  Val  Ser  Arg  Gly  Val  Gly
                        165                     170                     175

Phe  Ile  Arg  Phe  Asp  Lys  Arg  Ile  Glu  Ala  Glu  Ala  Ile  Lys  Gly
                   180                      185                     190

Leu  Asn  Gly  Gln  Lys  Pro  Ser  Gly  Ala  Thr  Glu  Pro  Ile  Thr  Val  Lys
              195                      200                     205

Phe  Ala  Asn  Asn  Pro  Ser  Gln  Lys  Ser  Ser  Gln  Ala  Leu  Leu  Ser  Gln
         210                      215                     220

Leu  Tyr  Gln  Ser  Pro  Asn  Arg  Arg  Tyr  Pro  Gly  Pro  Leu  His  His  Gln
    225                      230                     235                      240

Ala  Gln  Arg  Phe  Arg  Leu  Asp  Asn  Leu  Leu  Asn  Met  Ala  Tyr  Gly  Val
                        245                     250                     255

Lys  Arg  Leu  Met  Ser  Gly  Pro  Val  Pro  Pro  Ser  Ala  Cys  Ser  Pro  Arg
                   260                      265                     270

Phe  Ser  Pro  Ile  Thr  Ile  Asp  Gly  Met  Thr  Ser  Leu  Val  Gly  Met  Asn
              275                      280                     285

Ile  Pro  Gly  His  Thr  Gly  Thr  Gly  Trp  Cys  Ile  Phe  Val  Tyr  Asn  Leu
         290                      295                     300

Ser  Pro  Asp  Ser  Asp  Glu  Ser  Val  Leu  Trp  Gln  Leu  Phe  Gly  Pro  Phe
    305                      310                     315                      320

Gly  Ala  Val  Asn  Asn  Val  Lys  Val  Ile  Arg  Asp  Phe  Asn  Thr  Asn  Lys
                        325                          330                     335

Cys  Lys  Gly  Phe  Gly  Phe  Val  Thr  Met  Thr  Asn  Tyr  Asp  Glu  Ala  Ala
                   340                      345                     350

Met  Ala  Ile  Ala  Ser  Leu  Asn  Gly  Tyr  Arg  Leu  Gly  Asp  Arg  Val  Leu
              355                      360                     365

Gln  Val  Ser  Phe  Lys  Thr  Asn  Lys  Ala  His  Lys  Ser
    370                      375                     380
```

METHODS AND COMPOSITIONS USEFUL IN THE RECOGNITION, BINDING AND EXPRESSION OF RIBONUCLEIC ACIDS INVOLVED IN CELL GROWTH, NEOPLASIA AND IMMUNOREGULATION

BACKGROUND OF THE INVENTION

1. Field of the Invention

This invention relates to proteins which contain amino acid sequences that bind to 3'-untranslated regions of mRNAs, particularly mRNA sequences containing "instability sequences" (Shaw et al, Cell (1986) 46: 659–667).

2. Discussion of the Background

General features of primary sequence that characterize RNA- and DNA-binding proteins have begun to become apparent. The helix-turn-helix (Pabo et al, Annu. Rev. Biochem., (1984) 53: 293–321) and zinc-binding finger (Evans et al, Cell 1988) 52: 1–3) arrangements have both been observed as structural features of sequence-specific DNA-binding proteins. In eukaryotes, the homeobox domain seems to represent a widespread primary sequence motif for specific DNA-binding (Levine et al, Cell (1988) 55: 537–540; Robertson, Nature (1988) 336: 522–524, and references therein), and the members of the steroid hormone receptor superfamily of DNA-binding proteins utilize a common motif which forms zinc-binding fingers (Evans, Science (1988) 240: 889–895).

Early on RNA-binding proteins were less well studied than DNA-binding proteins; general features of RNA-binding proteins were not evident until the recognition of an amino acid octamer present in four proteins associated with mammalian nuclear RNAs (Adam et al, Mol. Cell Biol. (1986) 6: 2932–2943). The recognition of RNA by proteins has appeared to the inventors to be a key reaction in the regulation of expression of the genetic material of all cells.

One of the present inventors has studied RNA binding proteins of this group for many years and in 1983 isolated the first eukaryotic recombinant cDNA member of this family of proteins that encodes the human La RNA binding protein (Chambers et al, Proc. Natl. Acad. Sci. (USA) (1985) 82: 2115–2119; Chambers et al, J. Biol. Chem. (1988) 263: 18043–18051).

Subsequently, the observation by Dreyfuss and coworkers (Adam et al, Mol. Cell. Biol. (1986) 6: 2932–2943; Swanson et al, Mol. Cell. Biol. (1987) 1: 1731–1739) of an "RNP consensus" octamer in several eukaryotic proteins associated with RNA was an early indication that an amino acid sequence common among some RNA-binding proteins might exist.

Other publications by the Dreyfuss group (Dreyfuss et al, TIBS (1988) 13: 86–91) and from many other laboratories (Amrein et al, Cell (1988) 55, 1025–1035; Bell et al, Cell (1988) 55, 1037–1046; Bugler et al, J. Biol. Chem. (1987) 262: 10922-1-925; Chambers et al (1988), ibid; Deutscher et al, Proc. Natl. Acad. Sci. (USA) (1988) 85: 9479–9483; Goralski et al, Cell (1989) 56, 1101–1108; Keene, J. D., J. Autoimmunity (1989) 2: 329–337; Merrill et al, J. Biol. Chem. (1988) 263, 3307–3313; Sachs et al, Mol. Cell. Biol. (1986) 7, 3268–3276) noted the presence of related sequences surrounding the octamer and speculated that these regions might participate in RNA binding. It was not known at that time however whether these sequences might endow specific as opposed to nonspecific recognition of RNA or if discontinuous regions involving long-range interactions within these proteins might be required for RNA binding.

Some authors speculated that the octamer and its surrounding residues constituted an RNA binding domain and Dreyfuss and coauthors (ibid) chose an arbitrary size of 100 amino acids. Their theory was based upon the occurrence of similar sequences in a set of proteins that were all thought to be associated with RNA. Evidence for direct binding of such regions to specific RNA sequences was not available and no domains of proteins with binding activity were defined experimentally.

Included in this theory was the suggestion that the 70K U1 snRNP protein contained an RNA binding domain of 93 amino acids from positions 94 to 186. Other investigators (Theissen et al, EMBO J. (1986) 5: 3209–3217) had speculated that a different region of the 70K U1 snRNP protein encompassing amino acid residues 241 to 437 as well as the same region speculated by Dreyfuss were either one or both involved in RNA binding. These speculations were based upon the relationship of the highly basic (positively charged) region at amino acids 241 to 437 of 70K protein to regions of other proteins (e.g., protamines and histones) known to bind nucleic acid. No experimental evidence was available to support these suggestions.

Although the 70K protein is one of ten proteins known to be associated with the U1 snRNP complex (Pettersson et al, J. Biol. Chem. (1984) 259: 5907–5914), there was no evidence of specific RNA protein contact between the 70K protein and any RNA species until the discovery of a specific binding of the 70K protein to U1 RNA. Furthermore, of the other members of this group of proteins studied in our laboratory, as well as, in many other laboratories, none was shown to directly bind to a specific RNA sequence until one of the present inventors discovered the sequence-specific interaction between 70K U1 snRNP protein and U1 RNA.

The region of the protein involved in this specific binding involves a different amino acid sequence of 70K protein than that speculated by Theissen et al or by Dreyfuss et al. In fact, one of the sequences proposed by Theissen as being responsible for RNA binding actually interferes with the detection of specific binding activity.

In addition, the discovery of the precise RNA binding domain of the 70K protein includes additional important amino acid sequences not previously recognized by the theory of Dreyfuss et al, by the published work of other workers mentioned above or by some of the inventors themselves in their earlier studies of La (Chambers et al, ibid) and the 60 kD Ro (Deutscher et al, ibid) protein members of the group.

RNA binding proteins are now known to be involved in the control of a variety of cellular regulatory and developmental processes, such as RNA processing and compartmentalization, mRNA translation and viral gene expression. Some proteins that recognize and bind RNA can be classified into families based upon primary sequence homology, as well as higher order structure.

The family of RNA binding proteins containing an RNP consensus octamer and an 80 amino acid motif implicated in RNA recognition (RRM) has been the subject of intense investigation. Query et al, Cell (1989) 57: 89–101; Kenan et al, Trends Biochem. Sci. (1991) 16: 214–220. Based upon crystallographic and NMR spectroscopic studies of the U1 RNA binding domain of the U1 snRNP-A protein a model of the tertiary structure has been derived. The tertiary structural model together with RNA binding studies have led to the suggestion that the RNA binding surface resides on a monomeric unit with four anti-parallel β-strands which contains solvent exposed aromatic and basic residues. Kenan et al (1991) supra. Additional biochemical data have demonstrated that a determinant of RNA binding specificity resides in a loop which connects two β-strands. Bentley et al, *Mol. Cell. Biol.* (1991) 11: 1829–1839.

More than forty members of the RRM superfamily have been reported to date, the majority of which reside in all tissues and are ubiquitously conserved in phylogeny. Kenan et al (1991) supra. Tissue-specific members of the RRM family are less common, including X16 which is expressed in pre-B cells, Bj6 which is a puff-specific Drosophila protein and elav (embryonic lethal abnormal vision) which is neuronal-specific in Drosophila. For some RRM proteins the natural RNA ligands have been identified or surmised, but the RNA-binding sequences are not known in most cases.

The RNA ligands for the tissue-specific RRM proteins have not been reported and may prove difficult to determine because of their specialized roles in certain developmental processes. However, in order to understand their functions in cellular RNA metabolism and development, it will be essential to identify the RNA sequences to which they bind.

Oncogenes encode growth factors that affect the rate of cell proliferation by influencing cell cycle events such as mitosis, intracellular signaling pathways and gene expression. Some well known oncogenes are c-src, c-myc and c-fos. Lymphokines, which affect the growth properties of immunoregulatory cells, also function as growth factors similar to oncogene products. Although oncogene products (oncoproteins) are central components in the origin of the neoplastic state, they work through a variety of complex and largely unknown pathways. Consequently, methods to specifically control the functions of oncoproteins have not materialized.

The more recent discovery of suppressor oncogenes (anti-oncogenes) has held promise for being able to counter the effects of oncogenes. Some examples of anti-oncogenes include: retinoblastoma (Rb) and p53. It is hoped that these factors can be used to counter the effects of oncoproteins and thus, provide new treatments for cancer. For example, breast tumors show a consistent defect in the p53 gene, thus, preventing p53 from countering the oncogenes that cause uncontrolled proliferation of the breast tumors. Unfortunately, there are likely to be dozens of anti-oncogenes, each being specific to a given type of cancer.

Accordingly, there is a strongly felt need for the discovery of materials generally useful in the recognition, binding and/or expression of ribonucleic acids involved in the growth, neoplasia and immunoregulation. Such materials would have many uses, including regulation of cell proliferation in vitro and in vivo, regulation of immune cell expression, stimulation of cell growth, the production of transgenic animals and cell lines for pharmaceutical tests of cancer, immune function and neurological diseases, diagnostic reagents for the detection of autoantibodies associated with cancers, in vivo targeting systems, in diagnosing pathology specimens of neuronal origin, and/or as genetic or neurogenetic disease markers involving malformations of the central nervous system.

SUMMARY OF THE INVENTION

Accordingly, one object of this invention is to provide novel proteins which can bind to mRNAs which encode oncoproteins or lymphokines.

It is another object of this invention to provide novel proteins which can bind to 3'-untranslated regions of mRNAs, particularly mRNA instability sequences, in eukaryotic cells.

It is another object of this invention to provide novel proteins, and their corresponding DNA and mRNA sequences, which can provide in cell cultures or in vivo modulation of the expression of oncogenes and/or lymphokine-encoding genes in eukaryotic cells.

It is another object of this invention to provide novel proteins, and their corresponding DNA and mRNA sequences, useful in the regulation of cell proliferation in cell cultures and in vivo.

It is another object of this invention to provide novel proteins, and their corresponding DNA and mRNA sequences, which can be used to take cells out of a proliferative state and into a state of differentiation.

It is another object of this invention to provide novel proteins, and their corresponding DNA and mRNA sequences, useful in the regulation of immune cell gene expression.

It is another object of this invention to provide novel proteins, and their corresponding DNA and mRNA sequences, useful for stimulating or suppressing mammalian cell growth.

It is another object of this invention to provide novel proteins, and their corresponding DNA and mRNA sequences, useful to produce transgenic animals and cell lines for pharmaceutical tests of cancer, immune function and/or neurological diseases.

It is another object of this invention to provide novel proteins, and their corresponding DNA and mRNA sequences, useful as diagnostic and/or therapeutic reagents for the detection or therapy of autoantibodies present in the body of a cancer patient.

It is another object of this invention to provide novel proteins, and their corresponding DNA and mRNA sequences, which can be used for the in vivo targeting of certain substances.

It is another object of this invention to provide novel proteins, and their corresponding DNA and mRNA sequences, useful for diagnosing pathology specimens of neuronal origin.

It is another object of this invention to provide novel proteins, and their corresponding DNA and mRNA sequences, useful as genetic or neurogenetic disease markers in the diagnosis and/or therapy of patients in need thereof.

The present invention which satisfies all of the above objects of the invention, and others as can be seen from the description of the invention given hereinbelow, relates to a novel protein, named Hel-N1 by the inventors, and related proteins, discovered by the inventors as being able to bind to 3'-untranslated mRNAs, including a sequence (the "instability sequence") that is uniquely present in the messenger RNAs that encode oncoproteins and lymphokines. The "instability sequence", discovered by Shaw et al (*Cell* (1986) 46: 659–667), resides in the 3'-noncoding region of mRNAs which encode oncoproteins and lymphokines. The present invention also provides DNA and mRNA sequences corresponding to Hel-N1 and the related proteins.

BRIEF DESCRIPTION OF THE FIGURES

A more complete appreciation of the invention and many of its attendant advantages will be readily obtained as the same becomes better understood by reference to the following detailed description when considered in connection with the accompanying figures.

FIG. 1 provides an amino acid sequence comparison of two Drosophila neuron-specific proteins, elav (SEQ ID NO: 1) and K3 (SEQ ID NO. 3), with that of the human counterpart, Hel-N1 (SEQ ID NO: 2). Open boxes represent the RNP2 consensus sequences of each RNA recognition motif, whereas, shaded boxes represent RNP1 consensus sequence. Vertical lines denote identical residues and hyphens denote gaps used to allow optimal alignment among the three sequences.

FIG. 2 provides a comparison of the three RRMs of elav (SEQ ID NOS: 14, 17 and 20), K3 (SEQ ID NOS: 15, 18 and 21), and Hel-N1 (SEQ ID NOS: 16, 19 and 22) with those of polypyrmidine tract binding protein (PPTB) (SEQ ID NOS: 4–6) (Garcia-Blanco et al, *Proc. Nat. Acad. Sci. (USA)* (1990) 87: 3082–3086, hnRNP-L (SEQ ID NOS: 7–9) (Pinol-Roma et al, *J. Cell. Biol.* (1989) 109: 2575–2587, Drosophila sex lethal (Sx1) (SEQ ID NOS: 10–11) and two other Drosophila proteins K1 (SEQ ID NO: 12) and K2 (SEQ ID NO: 13) as depicted by Kenan et al, (1991). Asterisks indicate key residues critical to the correct folding of the RNA binding domain.

Figure 3:
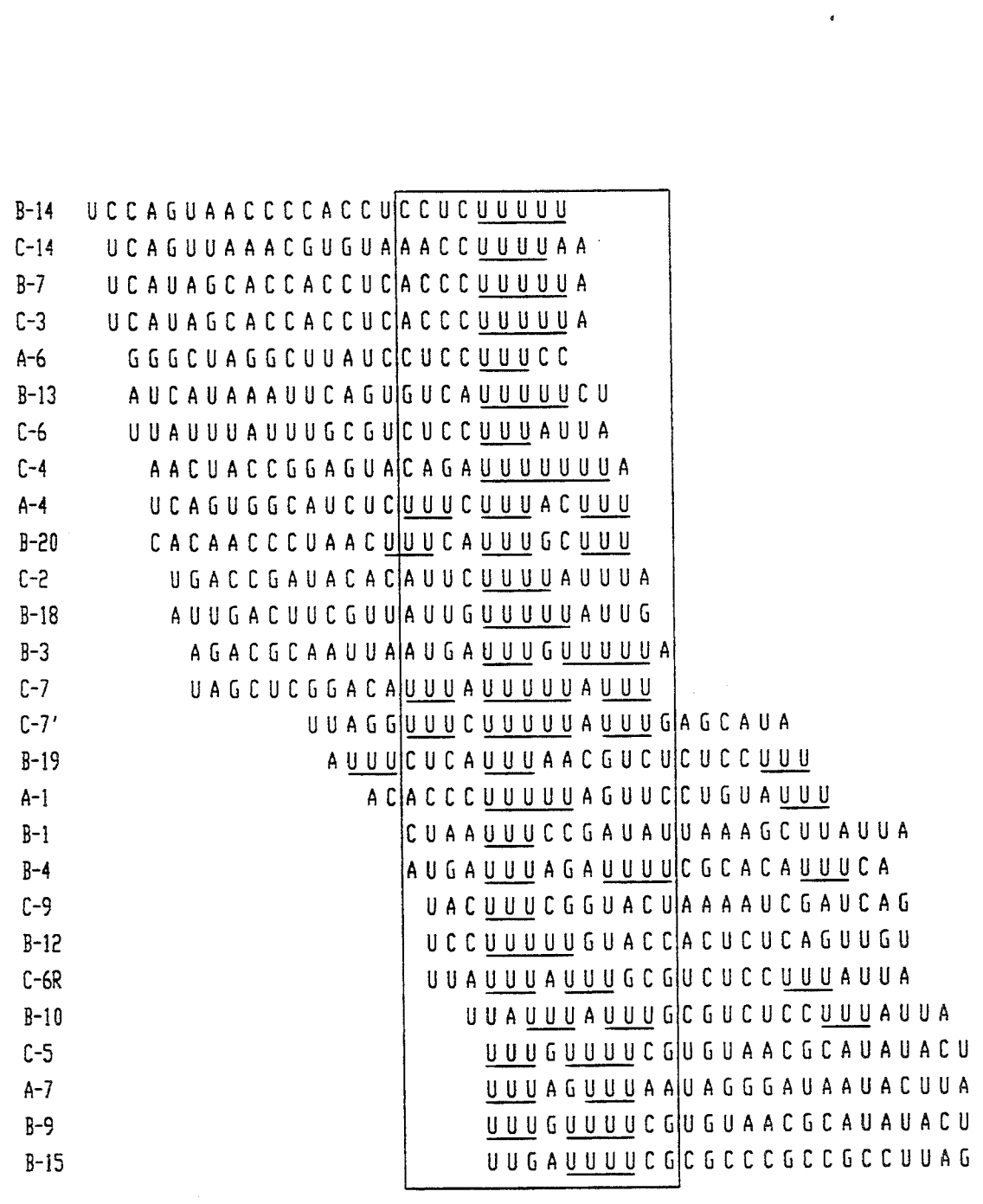

FIGS. 3 and 4 set forth RNA sequences selected to bind Hel-N1 using a random RNA selection procedure (Tsai et al *Nucl. Acids Res.*, (1991) 19: 4931–4936). FIG. 3 sets forth RNA sequences (SEQ ID NOS: 23–49), 25 nucleotides in length, which were identified from clones generated by reverse transcription and PCR amplification of selected RNAs. Twenty seven of the sequences consistently contained short stretches of uridylate residues interspersed with other nucleotides (boxed region). Two of the U-rich sequences were obtained twice. Two selected sequences (not shown) lacked the stretches of uridylates. FIG. 4 shows, among. FIG. 4 shows, among the sequences selected to bind Hel-N1 (FIG. 3), those that were found among the 3-UTR instability sequences indicated by Shaw et al, Cell (1986) 46: 659-667.

FIG. 6 sets forth the amino acid sequence (SEQ ID NO: 51) of a paraneoplastic encephalomyelitis antigen, HuD, reported by Szabo et al, *Cell* (1991) 67: 325–333.

FIG. 7 is a comparative diagram of elav subfamily members amino acid sequence.

DETAILED DESCRIPTION OF THE PREFERRED EMBODIMENTS

Figure 5:
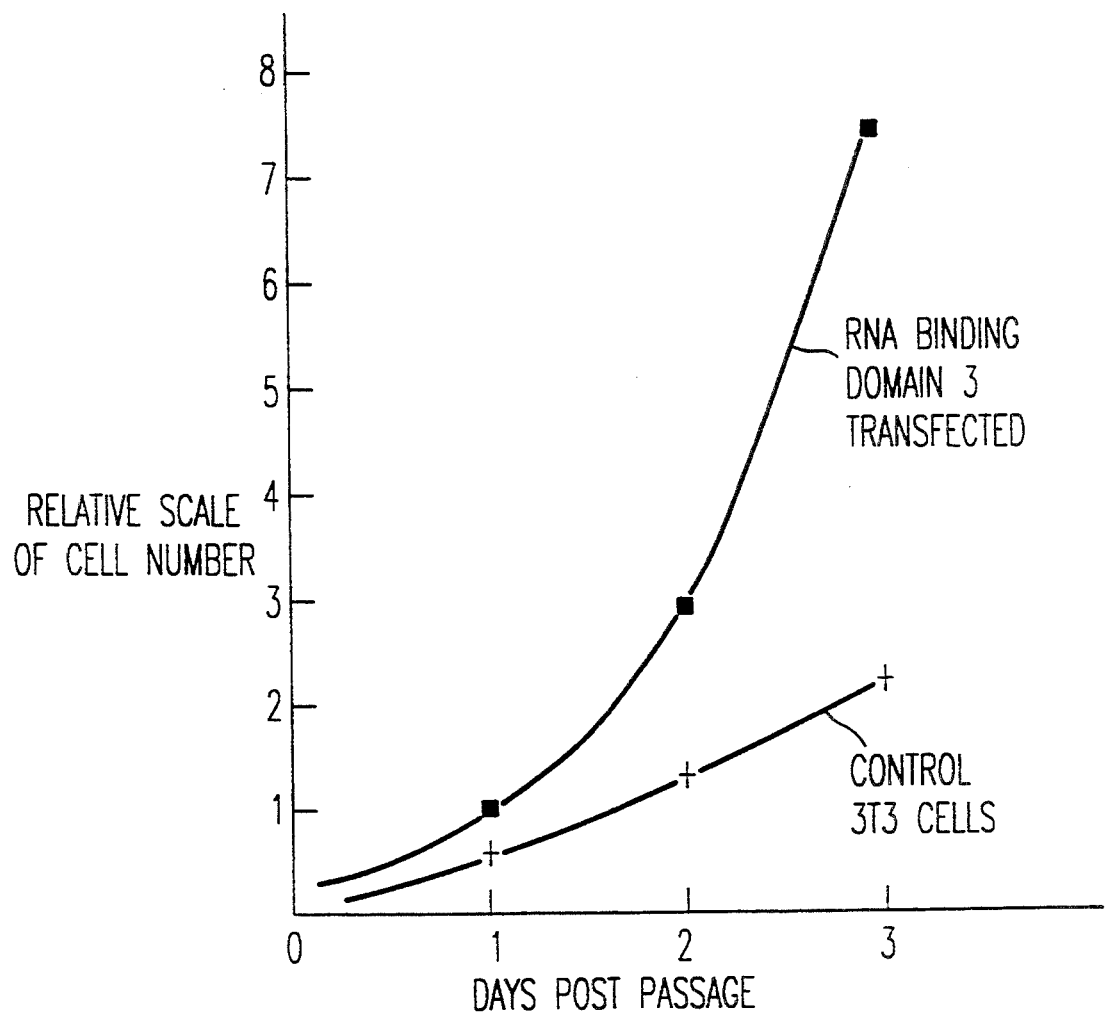
FIG. 5 illustrates a cellular growth curve obtained in accordance with the invention.

In this text, the following standard nomenclature is used.

TABLE 1

| Amino acid | Amino acid symbols. | |
|---|---|---|
| | Three-letter symbol | One-letter symbol |
| Alanine | Ala | A |
| Arginine | Arg | R |
| Asparagine | Asn | N |
| Aspartic acid | Asp | D |
| Asn + Asp | Asx | B |

TABLE 1-continued

| Amino acid | Amino acid symbols. | |
|---|---|---|
| | Three-letter symbol | One-letter symbol |
| Cysteine | Cys | C |
| Glutamine | Gln | Q |
| Glutamic acid | Glu | E |
| Gln + Glu | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The inventors have been isolating and characterizing RNA binding proteins, and studying their RNA-binding specificities. More particularly, as described in greater detail in application Ser. Nos. 07/536,943 and 07/436,779, filed on Jun. 12, 1990 and Nov. 15, 1989, respectively, both of which are hereby incorporated by reference, in studying the RNA-binding properties of the U1 RNA-associated 70K protein to elucidate regions of RNA-protein interaction, one of the inventors of the present invention, together with others, identified a central amino acid sequence involved in the specificity of gene expression at the level of pre-messenger RNA splicing in cells. While several structural motifs of proteins important in sequence-specific DNA-binding had been identified (e.g., helix-turn-helix and zinc-binding fingers) and two primary sequence motifs recently have been implicated directly in DNA-binding (homeoboxes and sequences within the steroid receptor family which form zinc-binding fingers), the structure or primary sequences of RNA-binding domains were not known prior to the invention of application Ser. Nos. 07/536,943 and 07/436,779.

Elav is known to be involved in the early development of the central nervous system (CNS). Homozygous mutations of this gene locus give rise to numerous structural defects and hypotrophy of the CNS leading to embryonic lethality. Its role in neuronal growth and differentiation of the Drosophila nervous system is also underscored by the temporal appearance of elav transcripts during the differentiation of neuroblasts into primitive neurons.

In probing for rat and human elav counterparts, the inventors relied on a novel approach of using degenerate primers designed to simulate the RNP-1 octamer sequence present in two of the three RRMs of Drosophila elav and thereby isolated cDNA encoding a novel neuron-specific protein, named Hel-N1 by them, from human brain by a combination of degenerate PCR probing and hybridization and found it to contain three RNA-recognition motifs (RRMs),. FIG. 1 provides the complete amino acid sequence of Hel-N1.

* The term recognition motif is used herein to designate an amino acid relationship; the term "RNA binding domain" designates a peptide segment shown to possess binding activity.

In in vitro studies they found that, in RNA binding, Hel-N1 prefers short stretches of uridylate residues and can bind the 3'-untranslated regions of c-myc, c-fos, and GM-CSF messenger RNAs, and that although Hel-N1 has three RRMs, only the third one (the most C-terminal binding domain situated between about amino acid positions 259 and 359) is responsible for mRNA 3'-untranslated region (which encompasses the instability sequence) binding activity. The inventors further discovered that full length Hel-N1, when transfected into a cell, caused cellular growth to cease. But, by contrast, and quite surprisingly, when only the third RNA binding domain was transfected into cells, the opposite result was obtained—the cells underwent rapid growth (as illustrated in FIG. 5).

It is not clear at this point whether transfection with the third RNA binding domain alone causes cellular transformation in the sense of an oncogene. RNA binding data obtained to date indicates that the single domain alone interferes with the ability of the full length Hel-N1 protein to bind in a multimeric fashion along the unstable oncoprotein or lymphokine mRNA. Thus, apparently the mRNA is rendered more stable and thus, more rapid proliferation results. In this sense, RBD3 may be a dominant negative suppressor of the instability function of Hel-N1.

The inventors' data demonstrates that the Hel-N1 protein binds as a multimer along the mRNA, presumably enhancing its instability and/or regulating its translatability and/or deadenylating it (thus, less proliferation). This protein may be responsible for the growth cessation of neurons.

Interestingly, recently Szabo et al (*Cell* (1991) 67: 325–333) reported the isolation of a cDNA encoding another human protein, termed HuD, based upon its reactivity with antisera from patients with paraneoplastic encephalomyelitis. But Szabo et al do not describe any binding by HuD to mRNA 3'-untranslated sequences, or mRNA instability sequences. HuD is also homologous to elav in the RRMs, but differs from elav, K3 and Hel-N1 at its amino terminus and other places (see FIG. 7. Thus, it appears that four members of this subfamily have been identified and more are likely to be discovered.

Due to the high level of homology between them, the segments of elav found between amino acid positions about 393 and about 483, of K3 found between amino acid positions about 345 and about 444, and of HuD found between amino acid positions about 280 and about 380 can be used in accordance with the invention in lieu of the third domain of Hel-N1. (The amino acid sequences of elav and of K3 are set forth in FIG. 1, that for HuD is set forth in FIG. 6.)

The present invention thus relates to the Hel-N1 protein, to its third domain and related elav K3 and HuD segments, and to the exploitation of any of these proteins and their binding reaction to the 3'-untranslated regions containing the instability sequence of oncoprotein and lymphokine mRNAs (Shaw et al, 1986) as well as to different structural fusions that can be produced to target these mRNAs for up or down regulation.

The present proteins, namely either full length Hel-N1 or its third domain, can be used to obtain a binding reaction between two ligands in a manner analogous to that described in application Ser. Nos. 07/536,943 and 07/436,779, noted supra. For example, any number of other adducts (RNA or protein) can be attached to either of these ligands to create novel and useful ribonucleoproteins, or a ribonuclease can be attached to the RNA binding domain 3 using known techniques to directly target any of these mRNAs for destruction.

The proteins of the present invention can therefore be used as therapeutic reagents to provide for either growth suppression or growth stimulation. Full-length Hel-N1 can be used to cause growth suppression of cultured cells, presumably mediated through effects on the stability of messenger RNAs encoding growth factors. In accordance with the present invention, one can alter the growth properties of cells in which oncogenes and lymphokine genes are overexpressed. Thus, cancer cells, which may be targeted by any known standard means, including gene therapy, liposome-mediated delivery, retrovirus-mediated infection or direct infusion with Hel-N1 DNA, RNA or protein will consequently be retarded in their growth.

Likewise, immune cells regulated by lymphokines, such as interleukins, interferons and others can be growth suppressed using Hel-N1. In this embodiment, leukemic and lymphocytic cells targeted by delivery of Hel-N1 DNA, RNA or protein to the bone, thymus or bloodstream using known techniques become incapacitated. For example, immune B or T cells overproducing autoantibodies or other harmful antibodies can be targeted using antigens or antibodies imbedded in lyposomes or other known carriers which in turn, deliver Hel-N1 DNA, RNA or protein as a growth suppressor to destroy their ability to proliferate. The cells producing the harmful antibodies become thus incapacitated and immunosuppressive therapy can be enhanced in a specific manner.

In these regiments, Hel-N1 DNA, RNA or protein can be injected directly into cancer patients using known techniques to affect tumor growth. Likewise it can be injected into patients to suppress the proliferation of immune cells. Thus, with many variations on these themes, it can be seen that delivery of Hel-N1 DNA, RNA or protein which can block cell proliferation by suppression of growth factor messenger RNAs is highly advantageous.

As noted above, the inventors have found that the third RNA recognition motif of Hel-N1, found between amino acid positions 259 and about 349 of the Hel-N1 amino acid sequence provided in FIG. 1, constitutes the core of the oncoprotein and lymphokine mRNA binding domain. This approximately 100 amino acid-long fragment is responsible for the specific instability sequence binding activity.

The inventors also made the startling discovery that expression of this domain, by itself, results in rapid proliferation of cells. This is a result opposite to that obtained by using full length Hel-N1. Expression of RNA binding domain 3 of Hel-N1 caused an eightfold increase in the growth of cultured cells after 3 days, as illustrated in FIG. 5. This is a striking alteration in a rate of proliferation. Thus, the RNA binding fragment of the growth suppression protein, Hel-N1, can itself be used to lead to the reverse effects, rapid cell growth.

Delivery of this fragment to tissue can be used to regenerate growth of cells in that tissue. One can use this embodiment to regenerate nervous tissue, heart tissue, skin and other tissues of limbs and organs. Likewise, RNA binding domain 3 can be delivered to tissues involved in wound healing and at other sites that are unable to be otherwise stimulated. Immune cells that produce autoantibodies and other factors needed for protection of the body can be growth stimulated using this invention.

Hel-N1 is an autoimmune protein in certain patients who show central nervous system manifestations of cancer called paraneoplastic cerebellar degeneration of (PCD), paraneoplastic encephalomyelitis (PE) or paraneoplastic sensory neuropathy (PSN). A therapeutic regiment could involve injection of Hel-N1 or peptides derived from Hel-N1 in order to block the immune effect or cellular immune recognition for properties in these diseases. Large amounts of pure Hel-N1 or its third domain are readily available using standard DNA cloning technologies or protein synthesis technologies. The purified protein can be used for immuno depletion of harmful autoantibodies or autoantibody—producing cells using methods of apheresis or dialysis.

The inventors also surprisingly discovered that full-length Hel-N1 can take cells out of a proliferative state and into a state of differentiation. Illustratively, whereas the third RNA binding domain of Hel-N1 was discovered to cause increased cell growth and the whole Hel-N1 protein discovered to cause cessation of cell growth, the inventors also observed that when certain neuroblastoma cells of (B104) were subjected to expression of whole Hel-N1 protein the cells developed an altered morphology. The cells became elongated like muscle cells and began to produce myotubules consisting of myosin and actin fibrils.

A cell derived from brain tissue was caused to enter an apparent myogenic pathway of differentiation by use of a protein of the present invention. This effect was due to the presence of a growth factor whose mRNA contained an instability sequence to which Hel-N1 was able to bind. In this case, the growth factor appears to be the Id protein which is known to suppress muscle differentiation. In the case of other similar growth factors, Hel-N1 may affect the differentiation of any cell which depends upon the continued expression of a growth factor encoded by an mRNA containing an instability sequence.

Thus, in another embodiment, Hel-N1 can be used in somatic or germline therapy to cause cells to undergo a desired pathway of differentiation. Hel-N1 has the further ability to control the balance between proliferation and differentiation that determines the developmental versus neoplastic consequences of gene expression.

The proteins of the present invention are also useful in therapeutic testing. An important need in the field of cancer research and immunology is for animal models which manifest altered growth properties or immune disregulation. Transgenic expression of polypeptides described in this application, using known techniques, can provide animals in which specific tissues or organs have been targeted to proliferate more rapidly or more slowly, thus allowing animal models of cancer or immune regulation to be produced. These animals are useful for testing the effect of chemotherapeutic drugs, radiation therapies, immune irregulatory agents, such as immunosuppressors and immunostimulators. Furthermore, Hel-N1 is itself an autoantigen to which patients with certain paraneoplastic diseases produce an autoantibody. The expression of Hel-N1 in transgenic tissues can allow production of an animal model for this autoimmune-type of cancer.

Proteins of the present invention are also useful in diagnostic applications. As a histological probe, Hel-N1 can be used to identify certain neuron types, such as granule cells or basket cells of the cerebellum. For example, in the pathology laboratory it is useful to stain cells with antibodies specific for Hel-N1 to determine the tissue origin of the specimen in question. Because Hel-N1 is present in certain neurons and not others, its presence in a tissue sample is an indicator of the type of tissue being examined.

Hel-N1 DNA constitutes a novel genetic marker for potential malformations of the central nervous system. For example, in the testing for genetic defects during prenatal examinations, many normal as well as abnormal markers are needed. For example, Hel-N1, in keeping with known oncogenes and antioncogenes, may be defective in patients suffering frmo natural cancers and leukemias. Full-length Hel-N1 DNA, RNA or protein may be used in the diagnosis and/or therapy of such individuals. Such therapy includes gene therapy, or targeted DNA, RNA or protein delivery. Hel-N1 is a useful, neuronal-specific probe. In testing for cystic fibrosis, Down's syndrome and similar genetic defects, one can get additional information on the status of CNS gene by monitoring Hel-N1 levels.

Thus in one embodiment, the present invention provides a polypeptide having the amino sequence of at least from the amino acid position 259 to 349 of Hel-N1 set forth in FIG. 1, and up to the whole amino acid sequence of Hel-N1. In another embodiment, the present invention provides a polypeptide which can be used to promote cell growth, where the polypeptide has the amino acid sequence of from amino acid position about 259 to about 349 of Hel-N1, or about position 393 to about position 483 of elav or about position 345 to about position 444 of K3, or about position 280 to about position 380 of HuD. In another embodiment, the present invention provides a polypeptide which can be used to suppress cell growth, and in particular expression of oncogenes and/or lymphokine encoding genes, by using a polypeptide having the whole amino acid sequence of Hel-N1.

In other embodiments, the present invention provides the corresponding DNA sequences and RNA sequences, optionally present in a liposome formulation, which may be either targeted or not targeted, or in a retroviral formulation, or in another formulation suitable for in vitro or in vivo delivery to cells or tissue. In other embodiments, these DNA and RNA sequences may be used in conjunction with gene therapy technology or to produce transgenic animals.

Another embodiment of the present invention relates to method for regenerating a mammalian tissue, including neuronal tissue, by administering to the tissue a polypeptide having the amino acid sequence of from about position 259 to about position 349 of Hel-N1 or the corresponding elav, K3 or HuD segments. The polypeptide may be administered to the tissue using any known means to deliver a polypeptide to a cell culture or in vivo to the cells of certain tissue, including gene therapy, liposome-mediated delivery, retrovirus-mediated infection, or direct infusion with the corresponding DNA, RNA or protein.

In another embodiment, the present invention is used to suppress the expression of an oncogene in a cell and/or of a lymphokine encoding gene in a cell, by causing the cell to express a polypeptide having about the whole amino acid sequence of Hel-N1. As with tissue regeneration, this may be achieved by using any standard means to cause the cell to express the desired polypeptide, including gene therapy, liposome-mediated delivery, retrovirus-mediated infection, or direct infusion with Hel-N1 DNA, RNA or protein. Particular oncogenes which may be targeted, include c-myc, c-fos or c-src, and others. Specific lymphokines which may be targeted in accordance with the present invention include GM-CSF, any interferon, or any interleukin, or others.

Hel-N1 and its associated DNAs and RNAs can also be used to produce transgenic animals and cell lines, using standard and known technologies, for pharmaceutical tests of cancer, immune functions and/or neurological diseases.

Having generally described this invention, a further understanding can be obtained by reference to certain specific examples which are provided herein for purposed of illustration only and are not intended to be limiting unless otherwise specified.

Hel-N1 and a rat cDNA, Rel-N1, appear to be homologous to Drosophila elav within the RNA recognition motifs; however, these proteins differ markedly in other regions. Analysis of mRNA expression in rat tissues demonstrated that Rel-N1, like elav, was specific to brain tissue. In situ hybridization localized Rel-N1 mRNA to neurons of the hippocampus and neocortex, but not to Purkinje cells, glial cells, or white matter.

The mRNA of the rat counterpart of elav was found to reside in a subset of neurons in the brain. It was not detected in glial cells or white matter and was found within the hippocampus and cerebral cortex of the rat. Using in vitro RNA binding methods, it was found that the human counterpart, Hel-N1 (Human elav-like Neuronal protein-1) could bind in vitro to the 3'-untranslated regions (3'-UTR) of certain mRNAs, including the mRNA "instability regions" of c-myc, c-fos and GM-CSF mRNAs.

These growth regulatory proteins are known to play important roles in cell proliferation, differentiation and immunoregulation. Thus, these observations show that Hel-N1, and perhaps other members of the elav subfamily, represent tissue-specific transacting factors involved in post-transcriptional mRNA metabolism.

Rat and human cDNA counterparts of the Drosophila neuronal protein, elav, were isolated using degenerate oligonucleotides, PCR, and library screening. RNAs capable of binding the human neuronal protein, Hel-N1, include 3'-UTRs of mRNAs encoding the oncoproteins, c-myc and c-fos and the lymphokine, GM-CSF. These RNA sequences encompass the "instability region" that is known to correlate with lability of these mRNAs (Meijlink et al, Proc. Nat. Acad. Sci. (USA) (1985) 82: 4987–4991; Shaw et al, Cell (1986) 46: 659–667; Jones et al, Mol. Cell Biol., (1987) 7: 4513–4521).

RNA binding results were obtained using recombinant Hel-N1 followed by: (1) selection of uridylate stretches from a degenerate pool of RNAs, (2) immunoprecipitation of c-myc, c-fos and GM-CSF mRNAs using two types of Hel-N1-specific antibodies, and (3) crosslinking to c-myc and GM-CSF 3'-UTR with uv light. The 3-UTR of these mRNAs are U-rich, but also contain other identifiable features of primary sequence. For example, the pentameric sequence, AUUUA defined by Malter Science (1989) 246: 664–666 and the octameric sequence, UUAUUUAU proposed by Caput et al, (1986), are common among the 3'-UTR of these mRNAs. These findings indicate that Hel-N1 and related proteins participate in the post-transcriptional regulation of unstable messenger RNAs.

Shaw et al Cell (1986) 46: 659–667, demonstrated a role for the A/U-rich 3'-UTR of protooncogene and lymphokine mRNAs in the instability of the RNA. In addition, they demonstrated that instability could be conferred to otherwise stable mRNAs by placement of the instability region in the 3'-UTR.

However, it should be noted that other regions of certain mRNAs, including c-myc, c-fos, histone and transferin receptor, have also been implicated in destabilizing yhr mRNA (reviewed by Cleveland and Yen, 1989; Atwater et al, 1990). Verma and coworkers (Meilink et al, 1985) demonstrated that removal of the 3'-UTR from c-fos mRNA resulted in increased levels of c-fos protein and cell transformation.

These studies show that regulatory events at the 3'-UTR are important for growth control. However, the A/U-rich 3'-UTR sequences span hundreds of nucleotides and the precise sequences involved in instability have not been identified. Recent work suggests that the AUUUA sequences are not required for instability, but that an upstream secondary structure in the 3'-UTR is more important. Thus, the role of the sequence elements within the 3'-UTR of these proto-oncogene and lymphokine mRNAs are not clearly defined at this time.

Proteins that interact with the 3'-UTR of oncoprotein and lymphokine mRNAs are poorly understood. Crosslinking with UV light and label transfer experiments by Vakalopoulou et al, Mol. Cell. Biol. (1991) 11: 3355–3364, noted a 32 kD protein that binds this region. Malter, Science (1989) 246: 664–666, observed a factor composed of three subunits, termed AUBF, in Jurkat cells that crosslinked to four repeats of the pentameric AUUUA sequence. More recently, Myer et al, Proc. Nat. Acad. Sci. (USA) (1992) found that small RNA transcripts from herpes simplex virus contain the AUUUA sequence and are capable of being UV crosslinked to the 32 kD protein from HeLa cell extracts. These findings suggest that there may be many proteins capable of recognizing sequences in the 3'-UTR. The binding specificity of Hel-N1 to the 3'-UTR of c-myc, c-fos, GM-CSF represents the only defined RNA-protein interaction in this region.

Using an in vitro RNA degradation assay Brewer (1991) identified and partially purified an activity termed, Auf, from human erythroleukemia cells that appears to be involved in instability of c-myc mRNA. Based upon a mobility shift assay, he postulated that proteins of 37 kD and a 40 kD present in these fractions were involved in binding to c-myc RNA. Although these factors were implicated in instability, they have not been characterized as to sequence or binding specificity.

Hel-N1 represents an amino acid sequence containing an RNA-binding domain that can recognize and bind to 3'-UTR of mRNAs containing the instability sequence. It is possible that Hel-N1 represents a neuron-specific counterpart of one of several proteins shown to bind A/U-rich 3'-UTR sequences in UV crosslinking studies. Given that it contains three different RRMS, it appears that Hel-N1 functions as a structural component of an RNP which interacts in the 3'-UTR through one RNA binding domain and carries another small RNA to that site. Alternatively, the RNA binding domains could perform a structural role in RNA bridging interactions as proposed for the U1 snRNP-A protein (Lutz-Freyermuth et al, Proc. Nat. Acad. Sci. (USA) (1990) 87: 6393–6397).

As an RNP or a bridging protein, Hel-N1 (or elav) may play a role in other post-transcriptional processes such as mRNA compartmentalization or translation. By this analogy, Hel-N1 may be involved in neuron-specific localization of mRNAs in the central nervous system.

Thus, members of the elav subfamily might recognize similar RNAs, but be functionally distinct based upon differences in their amino-terminal sequences. Expansion of the subfamily and determination of the tissue specificity and developmental regulation of each member will be required to address these possibilities.

Hel-N1, like HuD, was observed by the inventors to be reactive with an autoantibody present in the sera of patients with paraneoplastic disease, putting it in the category of other human autoantigens that are members of the RRM superfamily (Query et al, Mol. Cell. Biol. (1989), 9: 4872–4881). The potential to bind to oncoprotein mRNAs adds an element of intrigue because these patients are a subset of those inflicted with small lung cell carcinoma in which levels of c-myc protein are elevated. However, the mechanism of initiation of the autoimmune response to these self antigens remains as elusive as that of the systemic snRNP autoantigens. In addition, there is no evidence that Hel-N1 or HuD play a role in the derivation of the paraneoplastic syndrome or of small cell carcinoma. Additional information concerning the influence of Hel-N1 and related proteins on the production of cellular growth factors will be required to argue for such a link.

cDNAs encoding a variety of putative RNA-binding proteins were isolated by probing with degenerate oligonucleotides derived from conserved portions of the RRM. For members of the RRM family that contain multiple RRMs, oligonucleotides derived from the sequence of the RNP1 octamers were used.

Primers representing sense and antisense strands of the RNP 1 of RRM 1 and the RNP 1 of RRM 2 of elav DNA (Robinow et al, Science (1986) 242: 1570–1572) were used to probe mRNA from rat pup brain following reverse transcription with random primers. A PCR product was isolated and found to contain an ORF with an amino acid sequence termed, Rel-N1, which was, in turn, used to screen a human fetal brain library under high stringency conditions. A 2.2 kb DNA insert containing an open reading frame (ORF) of 359 amino acids was obtained. In vitro transcription and translation of the human cDNA produced a protein, termed Hel-N1, of the predicted size. Hel-N1 and Rel-N1 were identical in amino acid sequence and greater than 92% homologous in nucleic acid sequence.

Figure 2A:
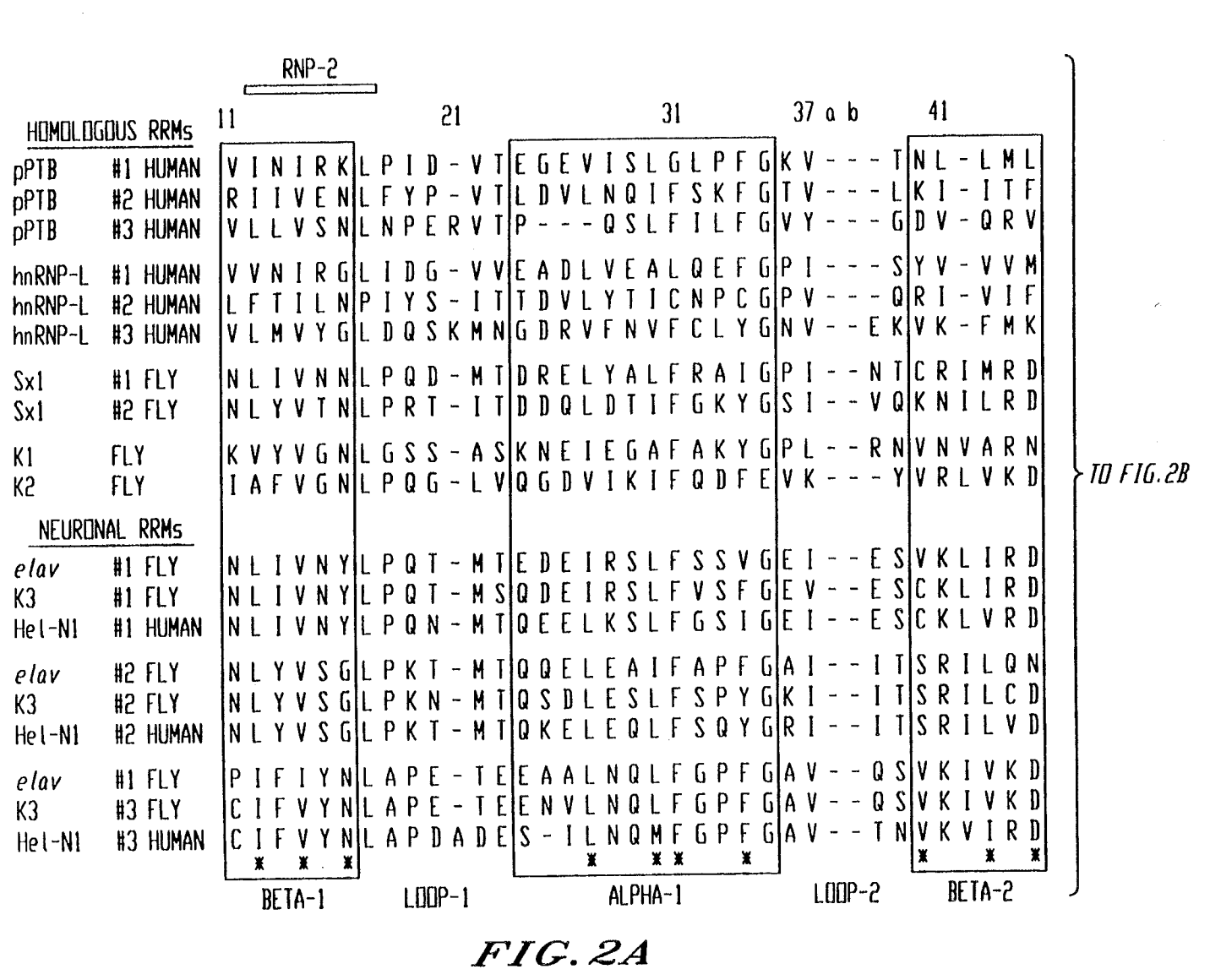
Figure 2B:
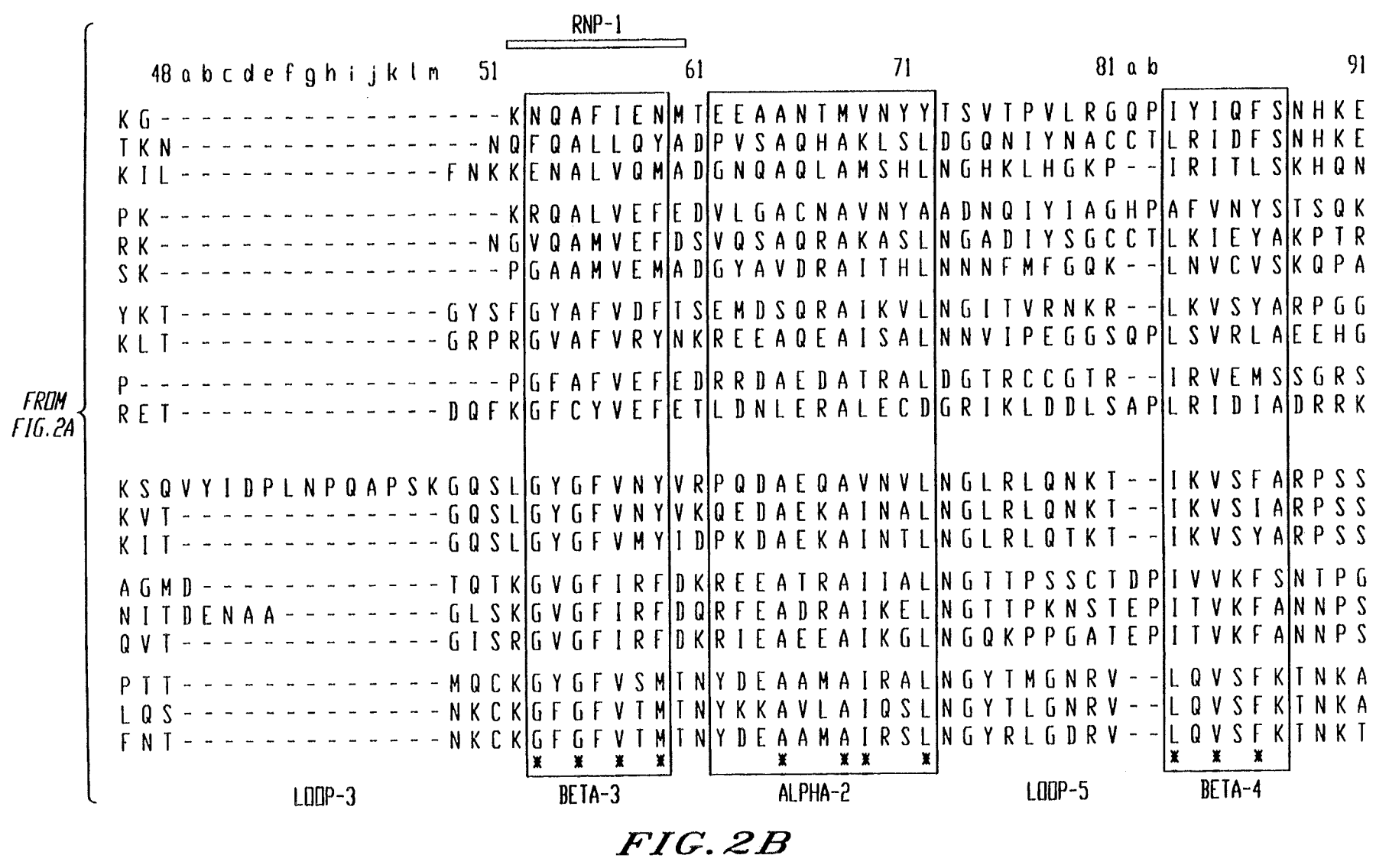

As shown in FIGS. 1 and 2, Hel-N1 contains three RNA binding domains as evidenced by RRMs 1, 2 and 3, which matched the structural criteria of Kenan et al (1991), supra, and each contained an RNP1 octamer (boxed and shaded) and an RNP2 hexamer (boxed) sequence. Sequence comparison of elav and a related Drosophila protein, K3, with Hel-N1, revealed strong similarities in the RRMs (FIGS. 1 and 2). On the other hand, Hel-N1 was only 76% the length of elav because the region amino terminal to the first RRM of the proteins demonstrated striking sequence differences (FIG. 1).

The amino terminus of Hel-N1 lacks the homopolymeric stretches of alanine, asparagine and glutamine seen in the amino termini of elav and K3, leaving it considerably shorter in length. This divergence is of unclear significance, especially in light of rescue studies done in Drosophila bearing the lethal mutation elavE5. These studies demonstrated that deletion of a 40 amino acid portion in the amino terminal does not prevent rescue from lethality. Thus, elav, Hel-N1 and K3 represent members of a subfamily of the RRM superfamily of RNA-associated proteins (Kenan et al, (1991), supra. This shows the existence of an elav-like subfamily of RNA binding proteins and, except for authentic elav, they can be designated by species as human (H) or rat (R) and tissue as neuronal (N) of origin.

Kenan et al, Trends. Biochem. Sci. (1991) 16: 214–220, have proposed that pPTB and hnRNP-L represent a distinct subset of the RRM superfamily of RNA binding proteins in that they lack the characteristic RNP 1 and RNP 2 sequences. Also evident in FIG. 2 are the sequence differences in loop 3 that connects $\beta$-strand 2 to $\beta$-stand 3 (RNP 1). Loop 3 has been described as highly variable among RRM family members (Bentley et al, Mol. Cell. Biol. (1991) 11: 1829–1839. In the case of the U1 snRNP-A protein, sequences residing in loop 3 were shown to affect the specificity of RNA recognition (Bentley et al, 1991; reviewed in Kenan et al, 1991); thus, representing one determinant of specificity. It is apparent that Hel-N1 differs from elav most strikingly in RRM 1, while RRMs 2 and 3 are highly similar (FIG. 2). This may indicate that the potential RNA-binding domains at RRM 1 of elav and Hel-N1 recognize very different RNA ligands.

Rel-N1 is neuron-specific

RNAs extracted from various rat tissues were analyzed by ribonuclease protection assays using Rel-N1 as probe. Protected bands were found only in RNA from rat brain; however, longer exposures revealed a small amount of RNA detectable in rat testes. To identify the specific neuroanatomic loci expressing Rel-N1 mRNA, 4% paraformaldehyde-fixed rat brain sections were hybridized with [35S]-labeled antisense RNA derived from the PCR fragment of Rel-N1 using the method of Fremeau et al, EMBO J (1990) 9: 3533–3538.

Data revealed that Rel-N1 mRNA was heterogeneously distributed in adult rat brain. Prominent hybridization signals were observed throughout all layers of the cerebral cortex and within the hippocampus. High levels of expression were observed in the CA3-CA4 fields of Ammon's Horn. In contrast, only low levels of expression were observed in the CA1 field of Ammon's horn and the granule calls of the dentate gyrus. Prominent hybridization signals were also observed throughout the thalamus and brainstem. Particularly intense hybridization signals were observed in the parafascicular and midline thalamic nuclei. In the cerebellum, only a small percentage of labeled cells were observed in the granule cell layer while only background labeling was observed over the molecular layer, the Purkinje cell layer, and the white reafter tracts. Grains were not observed over the choroid plexus, ependymal cells of the cerebral ventricles, and control sections hybridized with a sense-strand probe.

In sum, these data indicate that Rel-N1 mRNA is expressed most highly in the hippocampus and cerebral cortex, as well as in certain neurons in the granule cell layer of the cerebellum, but not in Purkinje cells of the cerebellum.

Our initial approach, given that the RNA binding ligands are not known for any of the four known elav sub-family members, was to use several standard RNA binding assays (Lerner et al, Proc. Nat. Acad. Sci. (USA), (1979) 76: 5495–5499) using total 32P labeled RNA isolated from HeLa, glioblastoma and neuroblastoma cells. In addition, in vitro RNA binding procedures which have been used effectively for other members of the RRM family of proteins (Query et al, Cell (1989) 57: 89–101; Lutz-Freyermuth et al, Proc. Nat. Acad. Sci.

*(USA),* (1990) 87: 6393–6397; Bentley et al, 1991) did not reveal a cognate RNA species for Hel-N1.

As an alternative approach, we used a random RNA selection procedure to define the RNA ligand site for Hel-N1. A synthetic oligodeoxynucleotide containing a stretch of 25 degenerate nucleotides was used to create a large heterogeneous pool of RNA sequences for selection of binding ligands (Tsai et al, *Nucl. Acids Res.* (1991) 19: 4931–4936). Binding of the degenerate RNA pool to recombinant Hel-N1, followed by immunoprecipitation of the complex using the epitope tag, gl0, was carried out as described previously (Lutz-Freyermuth et al, 1990; Bentley et al, 1991).

After three complete cycles of binding and selection, 30 independent clones, representing individual coimmunoprecipitated RNA species were evaluated by sequence analysis. The sequences of the bound RNAs showed a preponderance of uridylate residues in short stretches interrupted by other nucleotides. However, two of the 30 sequences (B-17 and B-5) did not contain this U-rich pattern. These variants were rare in the population and thus, may represent ligands of lower binding affinity. Alternatively, because Hel-N1 contains three potential RNA binding domains, these other sequences may represent ligands which were bound by one of the domains not involved in recognition of the U-rich regions. This possibility is compatible with the proposal that Hel-N1 may exist as an RNP that bridges between two or more RNAs via its multiple RRMs as proposed for the U1 snRNP-A protein (Lutz-Freyermuth et al, 1990).

This random RNA selection procedure has proved useful in our laboratory with other members of the RRM family of proteins to derive RNA ligand consensus sequences (Tsai et al, 1991), but in no other case has a U-rich sequence been selected. In the experiments using Hel-N1, RNA sequences with a U rich character were derived using the selection procedure, but a single consensus sequence was not evident.

The sequences selected from the in vitro RNA selection protocol were suggestive of biologically relevant sites known to exist in mammalian RNAs such as 3' UTRs in labile RNAs, the polypyrimidine tract near 3' splice junctions, sequence 5' of the polyadenylation signal, and in mitochondrial telomeres. The most striking feature was that short uridylate stretches flanked by either A, G or C could be located within the 3' UTRs listed by Shaw et al, *Cell* (1986) 46: 659–667 in their study of the instability sequences of proto-oncogene and lymphokine messenger RNAs. Thus, we conducted a series of direct RNA binding experiments to examine this possibility.

DNA constructs encoding portions of the 3' UTR of c-myc, GM-CSF, and c-fos mRNAs were used to synthesize radiolabeled transcripts for binding to recombinant Hel-N1 protein using our standard methods (Bentley et al, 1991). We utilized $^{32}p$ labeled transcripts corresponding to the 3' UTR sequences, as well as to a variety of unrelated RNAs. As with the RNA selection procedure used above, Hel-N1 was fused to the gl0 epitope for precipitation. c-fos, GM-CSF and c-myc transcripts were precipitable, while other transcripts were not precipitable.

The specificity of Hel-N1 binding to 3'-UTR of c-myc, GM-CSF, and c-fos 3' UTR was substantiated by the use of many control RNAs including total HeLa cell RNA, transcripts of various small RNAs, precursor mRNAs, various vector RNA transcripts and other RNAs. In addition, RNA binding was always in the presence of carrier transfer RNA and poly A (Query et al, 1989; Bentley et al, 1991).

Control transcripts for RNA binding specificity also included hY3 antisense RNA that contained a single AUUUA pentamer. This sequence has been suggested to represent the most conserved element present in the 3' UTR of the unstable protooncogene and lymphokine RNAs (Shaw et al, *Cell* (1986) 46: 659–667; Caput et al, (1986); Malter, *Science* (1989) 246: 664–666. Vakalopoulou et al, *Mol. Cell. Biol.* (1990) 11: 3355–3364, showed previously that the specificity for binding of these 3' UTRs to a 32 Kd protein present in Hela nuclear cell extracts resided in multiple copies of an AUUUA motif contained within a uridylate-rich region.

It should be noted that the hY3 RNA did not contain a uridylate-rich region surrounding the AUUUA. N-myc was also used as a control transcript because it contained a stretch of thirteen uridylates, but no AUUUA pentamer. None of these various control RNAs were significantly immunoprecipitated indicating that binding to Hel-N1 did not occur.

Among the control transcripts, we employed precursor mRNA-in-pieces (PIP vectors) which encode uridylate-rich stretches of RNA that are active in in vitro splicing and can be cross-linked with uv light to pPTB (Garcia-Blanco et al, 1990), supra. PIP transcripts also failed to bind Hel-N1. Several other RNA transcripts failed to bind Hel-N1 including coding regions of N-myc mRNA, U1RNA, a transcript encoding neomycin resistance, noncoding regions of U1 snRNP-70K mRNA, and coding regions of the dopamine 1 receptor.

In these studies, RNAs in the supernatants of the binding reactions were analyzed for the presence of intact non-bound RNA to rule out degradation. Although Hel-N1 binding to other untested U-rich sequences remains a possibility, its preference for the instability sequences at the 3' UTR of c-myc, GM-CSF, and c-fos mRNAs was compelling.

As an alternative confirmation of the RNA-binding specificity of Hel-N1 with the 3'-UTRs of these rapidly degraded mRNAs, label transfer experiments involving uv crosslinking with 32P labeled RNA were performed using standard procedures. HeLa cell nuclear extract and recombinant Hel-N1 in an *E. coli* extract were incubated with 32P labeled c-myc or GM-CSF mRNAs and exposed to UV light to mediate covalent cross-linking between the RNA and associated proteins. After cross-linking, excess RNA was digested with RNase A and analyzed on an SDS-acrylamide gel.

The label transfer to Hel-N1 revealed two predominant bands of 70 kD and 28 kD; similar results were obtained with GM-CSF (data not shown). The higher molecular weight band was found to be an artifact of IPTG induction, since control *E. coli* extracts lacking Hel-N1 also showed the 70 kD cross-linked band. The 28 Kd band (termed Hel-Ni) was 10 Kd smaller than the expected size of Hel-N1. While it is possible that the bound RNA or the cross-linking protocol caused Hel-N1 to migrate aberrantly, we observed that the 28 Kd band contained Hel-N1 epitopes (see below).

Direct label transfer experiments using HeLa cell extracts and radiolabeled c-myc mRNA demonstrated the ability to uv crosslink several proteins similar to that reported by Vakaloupoulu et al (1991). To determine whether Hel-N1 can compete with cross-linked proteins in the HeLa cell nuclear extract for binding to c-myc, increasing amounts of Hel-N1 were added prior to UV exposure. Neither the 32 kD protein identified by Valakopoulou et al (1991) nor hnRNP C protein (45 kD) diminished significantly upon addition of Hel-N1.

In addition, the 28 kD Hei-N1 band (Hel-Ni) appeared during the crosslink competition.

These results indicate that Hel-N1, the 32 kD protein, and hnRNP-C protein can bind simultaneously to the 3'-UTR of c-myc MRNA. On the other hand, a band of 65 kD was competed by Hel-N1, while E. coli extracts lacking Hel-N1 had no effect. The identity of the competed 65 kD protein remains unknown. These data suggest that while the HeLa 32 Kd protein and hnRNP C may share similar RNA binding characteristics with Hel-N1, their binding sites as defined by uv crosslinking are not identical.

Recent studies into several paraneoplastic neurologic disorders including paraneoplastic sensory neuropathy (PSN), paraneoplastic cerebellar degeneration (PCD), and paraneoplastic encephalomyelitis (PEM) have reported the identification of several antigens recognized by the sera of patients with these disorders (Dropcho et al, *Proc. Nat. Acad. Sci. (USA)* (1987) 84: 4552–4556; Anderson et a, *Neurology* (1988) 38: 1018–1026; Dalmau et al, *Ann.. Neurol.* (1990) 27: 544–557; Szabo et al, *Cell* (1991) 67: 325–333).

One such antigen, HuD, displays strong similarity to recombinant Hel-N1, but possesses important differences. Both HuD and Hel-N1 contain three RRMs which share approximately 70% overall homology. The major differences exist in the amino termini and in a stretch of thirteen amino acids between the second and third RRMs.

Using anti-HuD sera, we demonstrated cross reactivity with Hel-N1 by Western blotting. When used in the RNA binding protocol in place of the g1 0 serum, an anti-Hu serum was found to immunoprecipitate c-myc transcripts that bound to Hel-N1 in vitro. Control RNAs did not bind Hel-N1. Furthermore, four normal human sera lacked the ability to immunoprecipitate these mRNPs. These experiments demonstrate that the complex formed between HuD antibodies and Hel-N1 does not interfere with the ability of the protein to recognize its RNA ligand.

To confirm the HuD RNA binding assay, the label transfer experiments using cmyc 3'-UTR and g 10-Hel-N1 as described above were followed by immunoprecipitation of the 28 Kd Hel-N1'band with HuD sera. Normal human sera were always negative. In addition, the 70Kd E. coli band was not immunoprecipitated by any of these sera, as expected of the nonspecific *E. coli* protein. These data show that HuD sera can also immunoprecipitate a preformed complex of RNA bound to Hel-N1. Thus, Hel-N1, and presumably HuD, appear to possess autoantigenic epitopes that are distinct from the RNA-binding domain(s) that recognize the uridylates.

It is interesting to note that the 28 Kd band (Hel-N1') was immunoprecipitated with the HuD sera, but not with the glO serum or normal sera. Thus, it was assumed that the amino terminus was lost by cleavage. Estimation of the resultant size of Hel-N1' suggests that cleavage occurred at a site C-terminal to the first RRM, leaving a fragment containing RRMs 2 and 3. The source of this unexpected cleavage event is currently under investigation. These results suggest that the interaction between c-myc mRNA and Hel-N1 is specific to the second or third RRM; one of which may constitute the RNA binding domain.

Experimental Procedures
Cloning Rel-N1 and Hel-N1 by PCR and hybridization

Degenerate PCR primers were synthesized based on the first seven amino acids of the RNP1 consensus sequence in the first (sense) and second (antisense) RRMs of elav. Inosine residues were placed in positions degenerate for all 4 nucleotides and Eco R1 restriction sites were placed at the 5' end of each oligonucleotide. cDNA was prepared by reverse transcribing total cytoplasmic RNA from a Sprague-Dawley rat pup brain according to the manufacturer's specifications (Cetus ®): 6 mg total RNA, 1 mM dNTPs, 100 picomoles of random hexamers (Pharmacia ®), GeneAmp buffer, 20 U RNASIN (Promega ®), 200U BRL reverse transcriptase. 40 cycles of PCR amplification were carried out using an annealing temperature of 37 and an extension temperature of 55 C. (cycles 1–4) and 72 (cycles 540). A PCR product of 281 bp was purified on a 1% agarose gel using Geneclean ® (Bio 101) and subcloned into a TA vector (in Vitrogen ®). The clone Rel-N1, was sequenced and found to have a high degree of homology with elav, including a 100% homologous RNP2 consensus sequence within the second RRM.

A random primed cDNA probe was generated using Rel-N1 and used to screen a λZAPII human fetal brain library (Stratagene ®). Seven positive plaques were isolated from an initial population of 500,000 phage screened using the following hybridization conditions: 50% formamide, 6× SSC, 0.1% SDS and 0.01% Blotto. Filters were hybridized for 18 hours at 42 C. and then washed two times at room temperature (10 minutes each) in 2×SSC/0.1% SDS followed by a final wash at 65 C. in 0.2xSSC0.1% SDS for 45 minutes. The Bluescript ® plasmids of the positive phage were then isolated according to the manufacturer's specifications (Stratagene ®).

Sequencing Hel-N1 cDNA

EcoR1 inserts within the Bluescript ® plasmids were sequenced by exonuclease digestion and primer extension using the dideoxynucleotide chain termination with a modified T7 DNA polymerase from the Sequenase system (USB). Oligonucleotides were synthesized on an Applied Biosystems ® 391 DNA synthesizer.

Expression of Hel-N1 in *E. coli*

An inducible T7 RNA polymerase expression system (Rosenberg et al, (1987) *Gene,* 56, 125–135 was used for production of Hel-N1 protein. By using PCR mutagenesis, a conservative point mutation was introduced into the carboxy portion of the ORF to delete an NcoI site, such that the only NcoI site remaining was at the translation-initiation methionine. An NcoI-EcoR1 insert from this construct was then subcloned in frame into pET-3c containing the T7 12-amino acid (g10) sequence at the 5cloning site. After transfection of this construct into BL21(DE3)pLysS, the bacteria were induced with IPTG. The cells were washed twice in SM buffer and then resuspended in a small volume of *E. coli* lysis buffer (1 XTBS, 10 mM EDTA, 0.05% Tween, 3mM DTT and PMSF). Lysis was completed by freeze-thawing the cells. The extract was centrifuged at 10,000×g to remove insoluble debris. The amount of induction was evaluated by sodium dodecylsulfate-polyacrylamide gel electrophoresis and Western blotting as well as Coomassie staining.

In situ Hybridization

In situ hybridization was conducted on 4% paraformaldehyde-postfixed adult rat brain sections as previously described (Fremeau et al, *EMBO J* (1990) 9:

3533–3538). Briefly, adult Sprague-Dawley rats were anesthetized with 300 mg of sodium pentobarbital, and killed by decapitation. Brains were removed and frozen on an aluminum block cooled with liquid nitrogen. Frozen sections (10 u) were prepared in a cryostat, mounted onto room temperature slides (Onasco Biotech ®; Houston, Tex.) and stored at −70° C. until processed for in situ hybridization.

Tissue sections were thawed and fixed for 10 min in 4% paraformaldehyde in phosphate-buffered saline at 4° C. The sections were then rinsed in 2×SSC, covered with a minimal volume of 2×SSC, and illuminated with a germicidal UV-lamp (30W, wide spectrum UV light) for 5 min at a distance of 30 cm. The sections were then rinsed in 2×SSC, and covered with prehybridization buffer (50% formamide, 0.6M NaCl, 10mM Tris-HCl (pH 7.5), 0.02% Ficoll, 0.02% polyvinyl pyrollidine, 0.1% bovine serum albumin, 1 mM EDTA (pH 8.0), 50 ug/ml salmon sperm DNA, 500 ug/ml yeast total RNA, 50 ugml yeast tRNA and stored at 50° C. for 1 hr.

Prehybridization buffer was removed, and the slides were covered with hybridization buffer (50% formamide, 0.6M NaCl, 10 mM Tris-HCl (pH 7.5) 0.02% Ficoll, 0.02% polyvinyl pyrollidone, 0.1% bovine serum albumin, 1 mM EDTA (pH 8.0), 10 ug/ml salmon sperm DNA, 50 ug/ml yeast total RNA, 50 ug/ml yeast tRNA, 10 mM dithiothreitol, 10% dextran sulphate containing 35S-labeled probes (2.5–5.0×10$^6$ cpm/ml; heat-denatured for 15 min at 65° C.).

Hybridization was performed for 16–18 hrs at 50° C. Following hybridization, the sections were washed for 60 min in 2×SSC at 50° C. and then treated with RNase A (50 ug/ml) for 60 min at 37° C. The sections were then washed in 2×SSC for 60 min at 50° C. followed by a final high stringency wash in 0.1×SSC, 14 mM b-mercaptoethanol, 0.15% sodium pyrophosphate for 3 hr at 50° C., the heat was then turned off and the slides were allowed to gradually cool to room temperature overnight. The hybridized sections were dehydrated through graded ethanols containing 0.3M ammonium acetate, vacuum dried, and dipped in Kodak ® NTB2 emulsion diluted 1:1 with H$_2$O. After 4–6 week exposure times, the slides were developed as previously described (Fremeau et al, 1990) and photographed under dark-field illumination with kodachrome 160 tungsten slide film (Kodak ®).

RNA Probes

Rel-N1 cDNA was excised from the TA vector and subcloned into pGEM-3Zf(+) and linearized. $^{35}$S (for in situ hybridization) or 32P (for RNAse protection assay) labeled single stranded antisense RNA probes were synthesized using T7 RNA polymerase in the presence of [35S]UTP (New England Nuclear ®) or [32P]UTP (ICN). Sense RNA probe, made in a similar way, was used as a control for the in situ hybridization experiments. Unincorporated nucleotides were removed by G50 Sephadex (Pharmacia ®) columns.

Ribonuclease Protection Assays

Total cellular RNA was prepared from various tissues of an adult male Sprague-Dawley rat according to standard methods. Assays were carried out using 15 ug of total RNA from each tissue source essentially as described by Zinn et al (1983) Cell, 34, 865–879. Protected fragments were electrophoresed on a denaturing 5% polyacrylamide gel. The integrity of the RNA was ascertained by protection assay using 32P labeled antisense RNA transcribed from mouse β-microglobulin cDNA.

RNA selection procedure

The RNA selection process was done according to the method described by Tsai et al (1991). Briefly, an oligodeoxynucleotide containing a T7 promoter sequence (T7Univ) at one end, followed by 25 degenerate nucleotides and then a reverse universal primer sequence (RevUniv) at the other end was used in a PCR reaction (1 min. 94, 1 min. 50, 2 min. 72 in 10 mM Tris-HCl (pH 8.3), 50 mM KCl, 1.5 mM MgCl$_2$, 0.01% gelatin, 0.1 mg of T7Univ and RevUniv primers, 200 mm dNTPs and 2.5 U of Taq DNA polymerase) to create double stranded template for transcription. RNA was synthesized using T7 polymerase using standard methods (Maniatis, 1990).

In binding conditions described previously (Query et al, 1989), the degenerate pool of RNA was then incubated with g10-Hel-N1 fusion protein which had been prebound to protein-A beads (Sigma) using the g10 antibody. The beads were subsequently washed 5 times with NT2 buffer, and the immunoprecipitated RNA was then phenol extracted and ethanol precipitated in the presence of 10 ug of carrier tRNA (Sigma ®). The RNA was resuspended in 10 ul of doubly distilled water, and 3 ul was used for PCR amplification under conditions described above. The T7 and RevUniv primers had Bam-H1 restriction sites incorporated in the 5' ends such that any multimer products were reduced to monomers with Bam-H1 digestion. The same process was then carried out two more times. After the final PCR amplification and Bam-H1 digestion, the product was subcloned into pGEM-3Zf(+) and sequenced.

Plasmids and mRNA transcripts

The 3' end of the GM-CSF gene (240 bp fragment between Nco I and Eco RI cleavage sites) inserted into the polylinker, pGem3 containing the 3' end of the human c-fos gene (250 bp Rsal-Tth111I) inserted into the Hinc II site, and pGem3 containing the NsiI-AflII fragment of the 3' end of the human c-myc gene were used. The plasmids were linearized as follows: GM-CSF in PSP64 was cut at BglII and transcribed with Sp6 RNA polymerase; pGEM 3 containing c-fos was linearized with Kpn 1 and transcribed with T7 RNA polymerase; pGEM3 containing c-myc DNA was linearized with BamHI and transcribed with Sp6 RNA polymerase.

Linearized plasmid DNA was transcribed with SP6 RNA polymerase for c-myc and GM-CSF, or T7 RNA polymerase for c-fos. These reactions were carried out in the presence of 1.25 mm ATP, CTP, GTP; 0.75 mm UTP, and 5 ul of 1 u Ci/ul 32P UTP.

RNA Binding to Hel-N1

For each binding reaction 4 mg of Protein A beads were washed three times in NT2 Buffer (150 mm NaCl, 50 mm Tris-HCl pH 7.4, and 0.05% NP40). 5 ul of rabbit anti-g10 antibody, or 20 ul of human serum, was incubated with Protein A for 10 minutes on ice and washed three times with NT2 buffer. 35 ul of Hel-N1 *E. coli* extract was then added and incubated for ten minutes on ice and washed three times with NT2 buffer. After the final wash, the protein complex was resuspended in 0.1 ml of RNA Binding Buffer and equimolar amounts of labeled transcripts were added.

After a 5 min. incubation at room temperature, the binding reaction was washed five times with NT2 buffer and resuspended in 0.1 ml of NT2 buffer. 0.1 ml of the supernatant from the first wash was saved and treated identically as the bound pellet. 0.1 ml of diethyl pyrocarbonate treated water was added as well as 13 ul of 5M NaCl and 1 ul of 10 mg/ml of tRNA. The reactions were PCI extracted and EtOH precipitated. The pelleted RNA was run on a 6% urea polyacrylamide gel.

UV Cross Linking

Hela cell nuclear extract was prepared as described by Dignam (1983) and label transfer from RNA to protein was carried out as described by Wilusz et al, *Cell* (1988) 52: 221-228. 500,000 cpm of labeled transcripts were incubated with 5 ug of nuclear extract in a total reaction volume of 10 ul. The reaction was performed in a microtiter plate and irradiated for 10 minutes on ice. RNase A was added for a final concentration of 1 mg/ml and incubated for 15 minutes at 37° C. The reactions were mixed with Laemmli buffer and run on a 10% SDS polyacrylamide gel.

Hel-N1 crosslinking was carried out as above, except that the protein was dissolved in a uv cross-linking buffer (20 mm Hepes, 1 mm $MgCl_2$, 60 mm KCl 10% glycerol). Competition experiments included 5 ug of Hela cell nuclear extract in the presence of increasing amounts of Hel-N1 maintaining a total reaction volume of 10 ul.

Cellular Growth

NIH 3T3 cells where transfected with a pBC vector derived from the CMV promoter containing DNA expression RNA binding domain 3 (RBD3) of Hel-N1 using the calcium phosphate method. Cells were co-transfected with a plasmid encoding resistance to neomycin and colonies were selected with neomycin in the growth medium. After approximately three weeks of selection cells were examined by immunoflorescents and found to express RBD3(=), while control cells transfected with neomycin resistance alone (+) did not express RBD3. Cells were counted at passage and planted on culture plates for determination of growth rate. At days 1, 2 and 3 a plate of each was sacrificed and the cell numbers determined. It was readily evident that those cells expressing RBD3 entered into rapid proliferation, while the control cells grew at the same rate as normal 3T3 cells.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A polypeptide consisting of the amino acid sequence of from amino acid position 259 to an amino acid position selected from the group consisting of amino acid positions 349 through 359 of Hel-N1 (SEQ ID NO:2).

* * * * *